(12) United States Patent
Fan et al.

(10) Patent No.: US 8,871,926 B1
(45) Date of Patent: Oct. 28, 2014

(54) SYNTHESIS OF PORPHYRIN NANOSTRUCTURES

(75) Inventors: Hongyou Fan, Albuquerque, NM (US); Feng Bai, Kaifeng (CN)

(73) Assignee: Sandia Corporation, Albuquerque, NM (US)

(*) Notice: Subject to any disclaimer, the term of this patent is extended or adjusted under 35 U.S.C. 154(b) by 501 days.

(21) Appl. No.: 12/892,342

(22) Filed: Sep. 28, 2010

(51) Int. Cl.
*C07D 487/22* (2006.01)

(52) U.S. Cl.
USPC .......................................................... 540/145

(58) Field of Classification Search
USPC .......................................................... 540/145
See application file for complete search history.

(56) References Cited

U.S. PATENT DOCUMENTS

| | | |
|---|---|---|
| 5,135,619 A | 8/1992 | Eida et al. |
| 5,814,370 A | 9/1998 | Martino et al. |
| 6,117,369 A | 9/2000 | Shelnutt et al. |
| 6,264,741 B1 | 7/2001 | Brinker et al. |
| 6,270,846 B1 | 8/2001 | Brinker et al. |
| 6,324,091 B1 | 11/2001 | Gryko et al. |
| 6,387,453 B1 | 5/2002 | Brinker et al. |
| 6,471,761 B2 | 10/2002 | Fan et al. |
| 6,627,048 B1 | 9/2003 | Shelnutt et al. |
| 6,808,867 B2 | 10/2004 | Doshi et al. |
| 6,913,832 B2 | 7/2005 | Fan et al. |
| 6,952,436 B2 | 10/2005 | Wirnsberger et al. |
| 7,125,497 B1 | 10/2006 | Tucker et al. |
| 7,132,163 B1 | 11/2006 | Shelnutt et al. |
| 7,223,474 B1 | 5/2007 | Shelnutt et al. |
| 7,253,004 B2 | 8/2007 | Vossmeter et al. |
| 7,332,264 B2 | 2/2008 | Doshi et al. |
| 7,338,590 B1 | 3/2008 | Shelnutt et al. |
| 7,374,599 B1 | 5/2008 | Shelnutt et al. |
| 2003/0232982 A1 | 12/2003 | Gong |
| 2007/0137701 A1 | 6/2007 | Sainte Catherine et al. |
| 2007/0153353 A1 | 7/2007 | Gruner |
| 2008/0003363 A1 | 1/2008 | Park et al. |
| 2008/0020317 A1 | 1/2008 | Park et al. |
| 2008/0247932 A1 | 10/2008 | Li et al. |
| 2008/0311513 A1 | 12/2008 | Park et al. |
| 2009/0226835 A1 | 9/2009 | Mayo et al. |
| 2010/0062260 A1 | 3/2010 | Takano et al. |
| 2010/0087337 A1 | 4/2010 | Dewitt |
| 2010/0111813 A1 | 5/2010 | Fan |
| 2010/0152030 A1 | 6/2010 | Bai et al. |
| 2010/0190633 A1 | 7/2010 | Bai et al. |

OTHER PUBLICATIONS

Drain et al., Porphyrin nanoparticles as supramolecular systems. New Journal of Chemistry, 2006, 30, 1834-43).*
Bai et al., Monodisperse Porous Nanodiscs with Fluorescent and Crystalline Wall Structure, Chem. Commun. Jun. 1, 2010, 46, 4941-4943.
Gong et al. Preparation and Characterization of Porphyrin Nanoparticles, J. Am. Chem. Soc. Nov. 6, 2002, 124, 14290-14291.
Hasobe et al., Ordered Assembly of Protonated Porphyrin Driven by Single-Wall Carbon Nanotubes. J- and H-Aggregates to Nanorods, J. Am. Chem. Soc. Aug. 6, 2005, 127, 11884-11885.
Hu et al., Three-Dimensional Self-Organization of Supramolecular Self-Assembled Porphyrin Hollow Hexagonal Nanoprisms, J. Am. Chem. Soc. Nov. 11, 2005, 127, 17090-07095.
Lee et al. Growth of Narrowly Dispersed Porphyrin Nanowires and Their Hierarchical Assembly into Macroscopic Columns, J. Am. Chem. Soc. Jul. 3, 2008, 130, 9632-9633.
De Luca et al. Self-Organizing Functional Materials via Ionic Self Assembly: Porphyrins H- and J-Aggregates on Synthetic Chrysotile Nanotubes, J. Am. Chem. Soc. Apr. 30, 2009, 131, 6920-6921.
Qiu et al. Evolution of Various Porphyrin Nanostructures via an Oil/Aqueous Medium: Controlled Self-Assembly, Further Organization, and Supramolecular Chirality, J. Am. Chem. Soc. Jun. 28, 2010, 132, 9644-9652.
Steinbeck et al. Interactions of Charged Porphyrins with Nonionic Triblock Copolymer Hosts in Aqueous Solutions, Langmuir Aug. 27, 2004, 20, 10399-10412.
Wang et al., Porphyrin Nanotubes by Ionic Self-Assembly, J. Am. Chem. Soc. Nov. 19, 2004, 126, 15954-15955.
Wang et al., Self Assembly and Self-Metallization of Porphyrin Nanosheets, J. Am. Chem. Soc. Feb. 10, 2007, 129, 2440-2441.
Wang et al., Self-Metallization of Photocatalytic Porphyrin Nanotubes, J. Am. Chem. Soc. Dec. 7, 2004, 126, 16720-16721.

* cited by examiner

*Primary Examiner* — Brian McDowell
(74) *Attorney, Agent, or Firm* — Fletcher Yoder P.C.; Kevin W. Beig

(57) ABSTRACT

The present disclosure generally relates to self-assembly methods for generating porphyrin nanostructures. For example, in one embodiment a method is provided that includes preparing a porphyrin solution and a surfactant solution. The porphyrin solution is then mixed with the surfactant solution at a concentration sufficient for confinement of the porphyrin molecules by the surfactant molecules. In some embodiments, the concentration of the surfactant is at or above its critical micelle concentration (CMC), which allows the surfactant to template the growth of the nanostructure over time. The size and morphology of the nanostructures may be affected by the type of porphyrin molecules used, the type of surfactant used, the concentration of the porphyrin and surfactant the pH of the mixture of the solutions, and the order of adding the reagents to the mixture, to name a few variables.

18 Claims, 25 Drawing Sheets

(Sn-TPyP)

(TiO-TPyP)

(VO-TPyP)

(Co-TPyP)

(Mn-TPyP)

(Fe-TPyP)

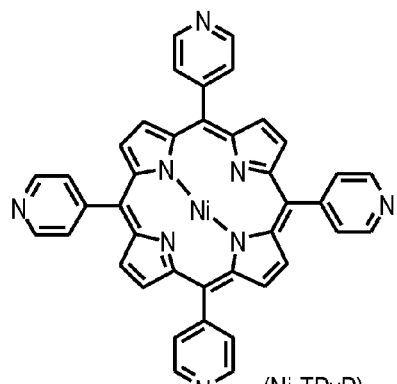
FIG. 2i (Ni-TPyP)
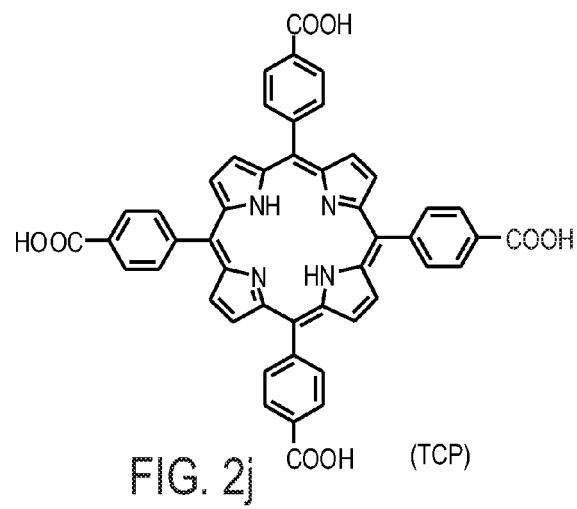
FIG. 2j (TCP)
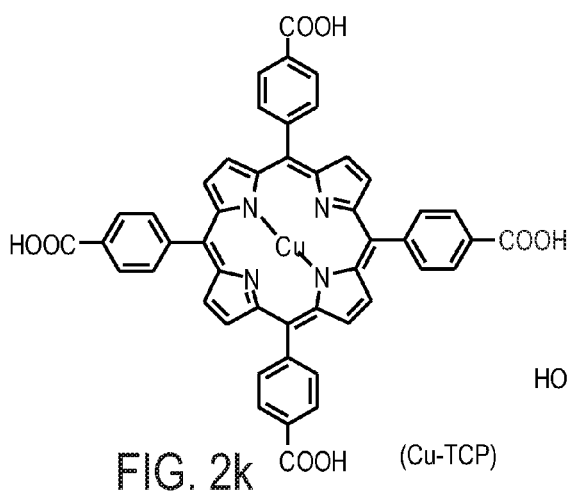
FIG. 2k (Cu-TCP)
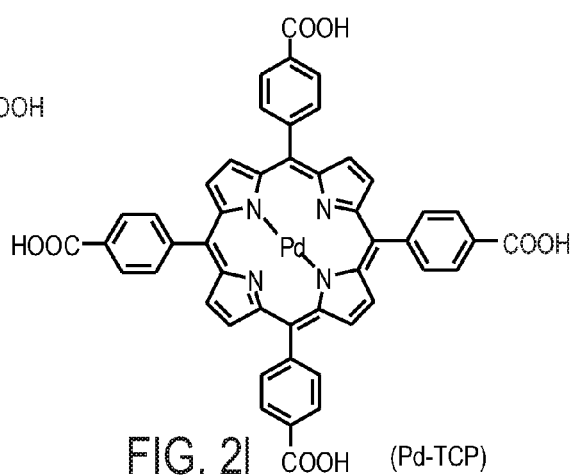
FIG. 2l (Pd-TCP)
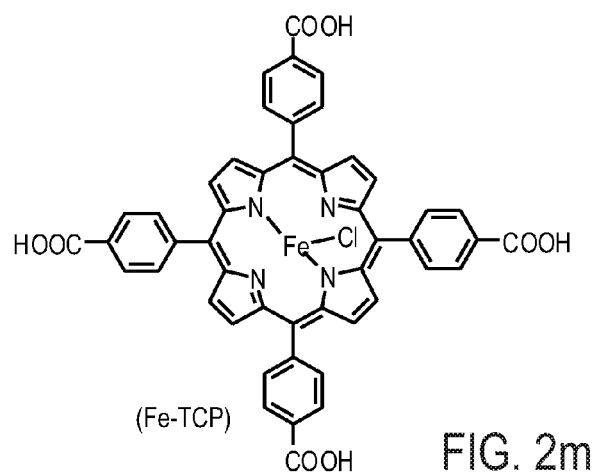
FIG. 2m (Fe-TCP)

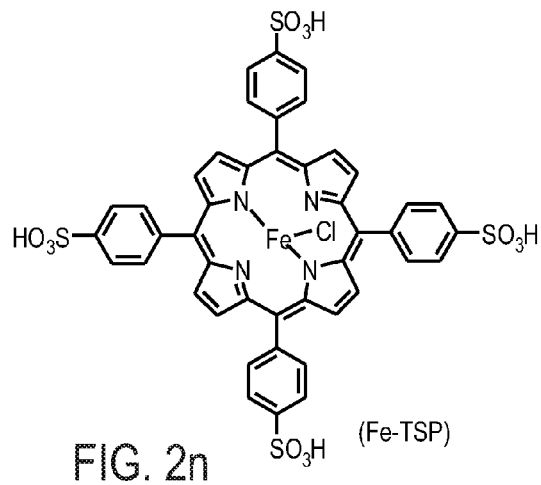
FIG. 2n (Fe-TSP)
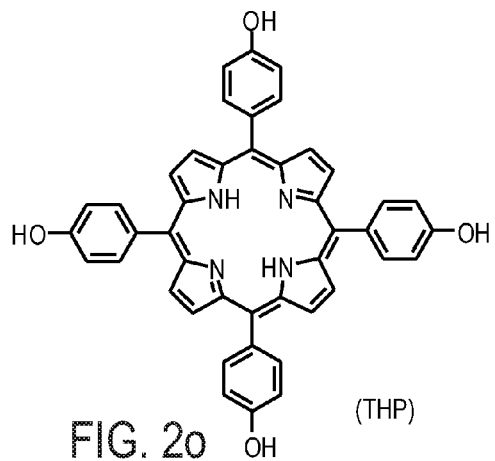
FIG. 2o (THP)
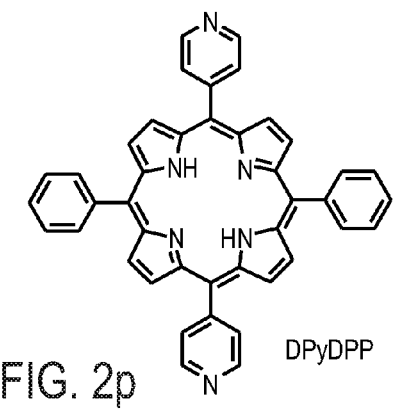
FIG. 2p DPyDPP
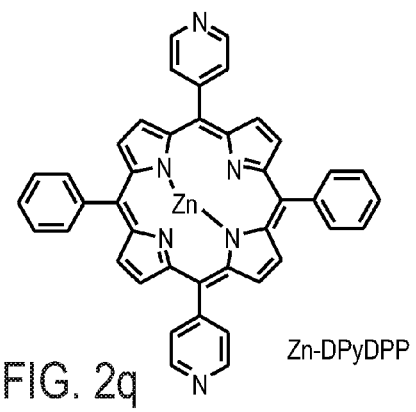
FIG. 2q Zn-DPyDPP
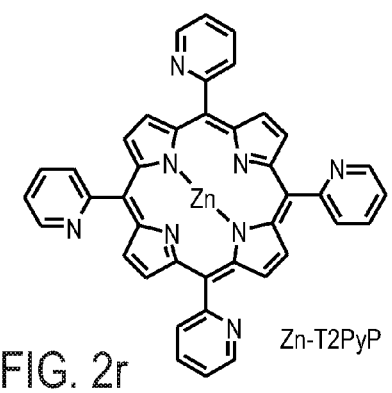
FIG. 2r Zn-T2PyP
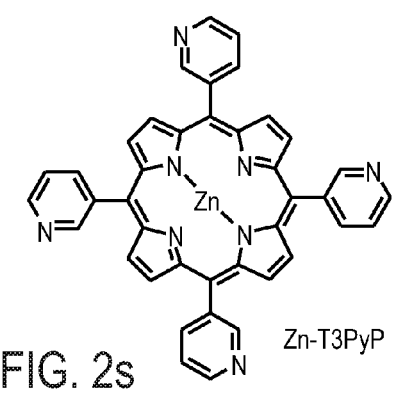
FIG. 2s Zn-T3PyP

SDBS

SDS $C_7CO_2Na$ $C_8SO_4Na$ $C_9CO_2Na$ $C_{10}SO_4Na$ $C_{10}SO_3Na$ $C_{12}SO_3Na$ docusate sodium

CTAB

MTAB

DTAB n-DTAB glycolic acid ethoxylate lauryl ether

Tween 20

Brij@35

P-123

PROTOPORPHYRIN IX ZINC(II)

PROTOPORPHYRIN IX

HEMATOPORPHYRIN IX DIHYDROCHLORIDE

H678

HEMIN FERRIPROTOPORPHYRIN IX CHLORIDE

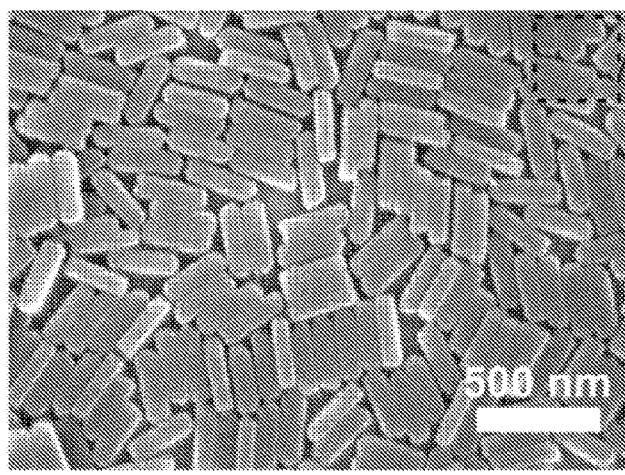
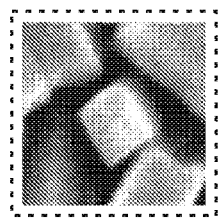
FIG. 15        FIG. 15a
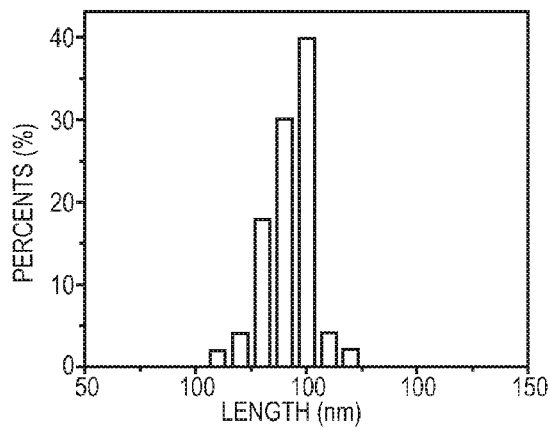
FIG. 16
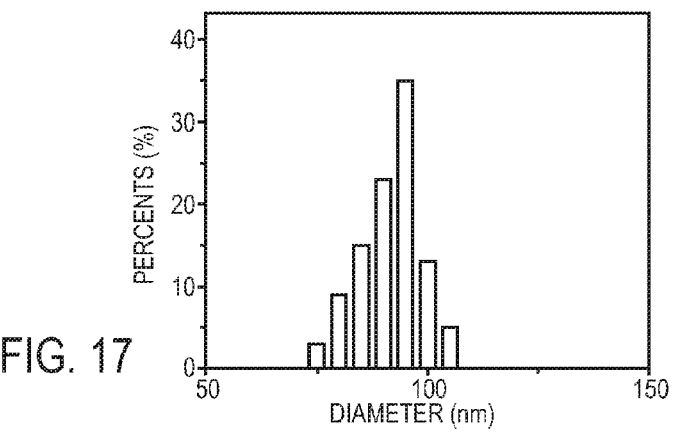
FIG. 17

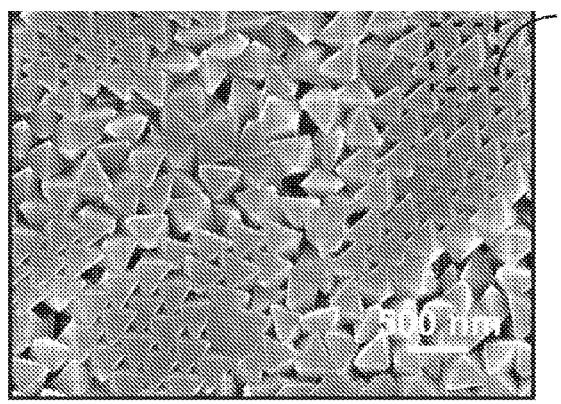 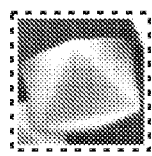
FIG. 25      FIG. 25a
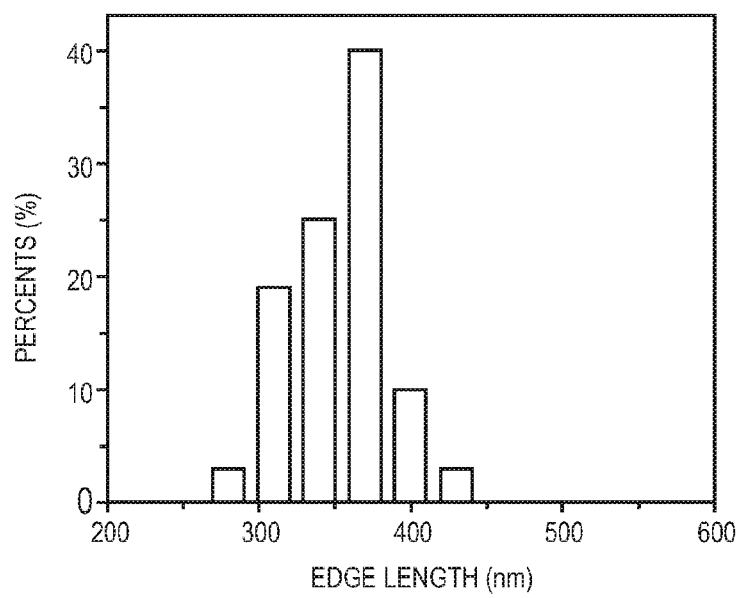
FIG. 26

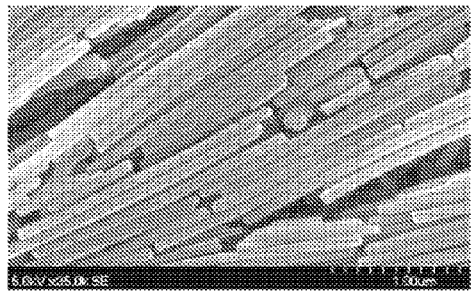 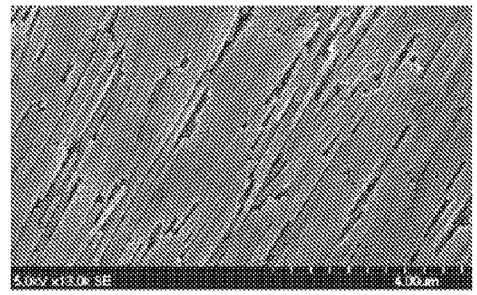
FIG. 37    FIG. 38
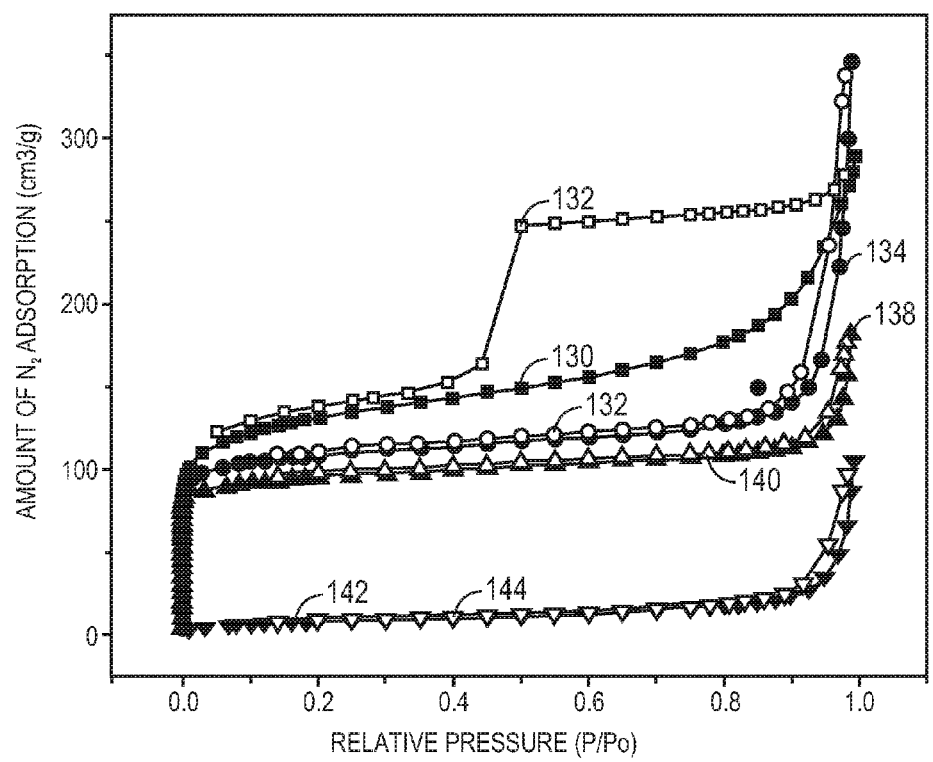
FIG. 39

SYNTHESIS OF PORPHYRIN NANOSTRUCTURES

STATEMENT REGARDING FEDERALLY SPONSORED RESEARCH AND DEVELOPMENT

This invention was made with United States Government support under Contract No. DE-AC04-94AL85000 between the Sandia Corporation and the United States Department of Energy. The United States Government has certain rights in the invention.

BACKGROUND

The present disclosure relates generally to methods for producing nanostructures, and more specifically, to a self-assembly method for producing porphyrin nanostructures.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Markets for certain areas of technology, such as electronics (e.g., computers, cellular phones, televisions), have benefited from technologies that allow the production of certain components at smaller scales. For example, the production of smaller electrical components allows an overall reduction in the size of electrical consumer products, a decrease in the amount of materials required for, and therefore the cost of, manufacturing such products, and an overall increase in capability (e.g., computing power) of the product. In typical manufacturing processes, small materials are produced from larger materials, which may be considered a top-down approach. Lithography, a process used to produce the millions of transistors in a computer processor, is one example. Unfortunately, present technologies, such as lithography, have begun to reach their limit to produce structures smaller than the microscale, such as on the nanometer scale.

Nanostructures, i.e., structures having at least one dimension less than about 1 micron, have potential application in a variety of areas such as nanoelectronics, nanophotonics, optics, sensors, catalysis, energy harvesting, bioengineering, and others. Moreover, materials can exhibit unique properties at the nanoscale that diminish at larger sizes. For example, nanostructures may be synthesized to have a wide variety of advantageous properties, such as electrical conductance, semi-conductance, resistivity, optical activity, optically-induced conductance, molecular recognition, catalytic activity, and so on that would otherwise not be present. In a general sense, these properties of nanostructures may be reminiscent of their single molecule counterparts, may result from a collective behavior of a larger assembled structure, or both.

In light of their unique properties and possible integration into existing technologies, it is widely recognized that there is a considerable need to produce nanoscale materials. An alternative approach to the top-down manufacturing techniques mentioned above is the bottom-up approach, where large structures are built from single molecules. Bottom-up approaches can be desirable when one or more dimensions of a nanostructure is tunable to obtain a particular benefit, or when structures are desired on a scale that is unreachable by other techniques. For example, the optical, electrical, chemical and/or other properties of nanostructures may be tuned by manipulating one or more of the nanostructure's dimensions, such as the length, diameter, and/or thickness of the nanostructure, as well as the chemical identity of the single molecules from which the nanostructure is formed. Moreover, bottom-up synthetic approaches can produce structures having a scale as small as a few angstroms ($10^{-10}$ m), or one ten-thousandth of the width of a human hair.

Molecular self-assembly is one example of a bottom-up approach for producing nanostructures. Synthetic self assembly methods, in a similar manner to biological systems, use one or more non-covalent interactions such as van der Waals forces, hydrogen bonding, aromatic $\pi$-$\pi$ stacking, and axial coordination to produce macromolecules from single molecules. However, unlike traditional synthetic methods where individual bonds can be formed and broken to control the exact molecular structure of a product, it can be difficult to predict and control the structure that is formed from a self-assembly process. Accordingly, there is a need for a method of self-assembly that is able to control the size and morphology of generated nanostructures.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

The present disclosure generally relates to self-assembly methods for generating porphyrin nanostructures. By confining the self-assembly, and therefore the growth, of such nanostructures by surfactant molecules, it may be possible to control their dimensionality and/or their morphology. For example, in one embodiment, a method is provided that includes preparing a porphyrin solution and a surfactant solution. The porphyrin solution is then mixed with the surfactant solution at a concentration sufficient for confinement of the porphyrin molecules by the surfactant molecules. In some embodiments, the concentration of the surfactant is at or above its critical micelle concentration (CMC), which allows the surfactant to template the growth of the nanostructure over time. The size and morphology of the nanostructures may be affected by the type of porphyrin molecules used, the type of surfactant used, the concentration of the porphyrin and surfactant, the pH of the mixture of the solutions, and the order of adding the reagents to the mixture, to name a few variables.

The method noted above is also applicable to the continued growth of pre-formed porphyrin nanostructures, for example when it may be desirable to change the morphology and/or size of an existing nanostructure. In one embodiment, a solution having the existing porphyrin nanostructure and a surfactant is prepared. The solution may be the mixture resulting from the self-assembly method mentioned above. If the self-assembly process of the nanostructure is substantially complete, the solution is then re-adjusted to conditions favorable for self-assembly. For example, the pH of the solution may be adjusted by adding acid or base, and fresh single porphyrin molecules may be added.

These methods may generally produce nanostructures with unique properties and well-defined and highly reproducible morphologies. As an example, the porphyrin nanostructures produced by the methods noted above may display photocatalytic behavior, photovoltaic behavior, fluorescence, gas storage capability, and may have size distributions that approach monodispersity. As an example of the photocatalytic activity of the nanostructures produced in accordance with the present embodiments, a method is disclosed wherein a porphyrin nanostructure is mixed with a reducing agent and a metal ion source. The mixture is then photoirradiated for a period of time to produce a nanostructure having a porphyrin inner core and a metal shell. The porphyrin nanostructure may be removed to generate a hollow metal nanostructure.

BRIEF DESCRIPTION OF THE DRAWINGS

Various aspects of this disclosure may be better understood upon reading the following detailed description and upon reference to the drawings in which:

FIG. 15 is an SEM image of a plurality of rectangular porphyrin nanorods produced using an embodiment of the method set forth in FIG. 4, in accordance with an aspect of the present disclosure;

FIG. 15a is an expanded view of a portion of the SEM image of FIG. 15 showing the rectangular ends of a portion of the plurality of rectangular porphyrin nanorods, in accordance with an aspect of the present disclosure;

FIG. 16 is a population histogram of the lengths of the plurality of rectangular porphyrin nanorods in the image of FIG. 15, in accordance with an aspect of the present disclosure;

FIG. 17 is a population histogram of the diameters of the plurality of rectangular porphyrin nanorods in the image of FIG. 15, in accordance with an aspect of the present disclosure;

FIG. 25 is an SEM image of a plurality of 3D porphyrin nanooctahedrons produced using an embodiment of the method of FIG. 24, in accordance with an aspect of the present disclosure;

FIG. 25a is an expanded view of a portion of the SEM image of FIG. 25 showing the edges of one of the 3D porphyrin nanooctahedrons, in accordance with an aspect of the present disclosure;

FIG. 26 is a population histogram of the edge lengths of the plurality of porphyrin nanooctahedrohs in the image of FIG. 25, in accordance with an aspect of the present disclosure;

FIG. 37 is an SEM image of a plurality of porphyrin nanorods prior to performing an embodiment of the method of FIG. 36, in accordance with an aspect of the present disclosure;

FIG. 38 is an SEM image of the plurality of porphyrin nanorods of FIG. 37 after performing an embodiment of the method of FIG. 36, in accordance with an aspect of the present disclosure;

FIG. 39 is a plot of nitrogen absorption and desorption as a function of relative pressure for porphyrin nanodiscs, porphyrin nanorods, hexagonal porphyrin nanorods, and porphyrin nanoplates produced using varying embodiments of the method of FIG. 1, in accordance with an aspect of the present disclosure;

DETAILED DESCRIPTION OF SPECIFIC EMBODIMENTS

Figure 1:
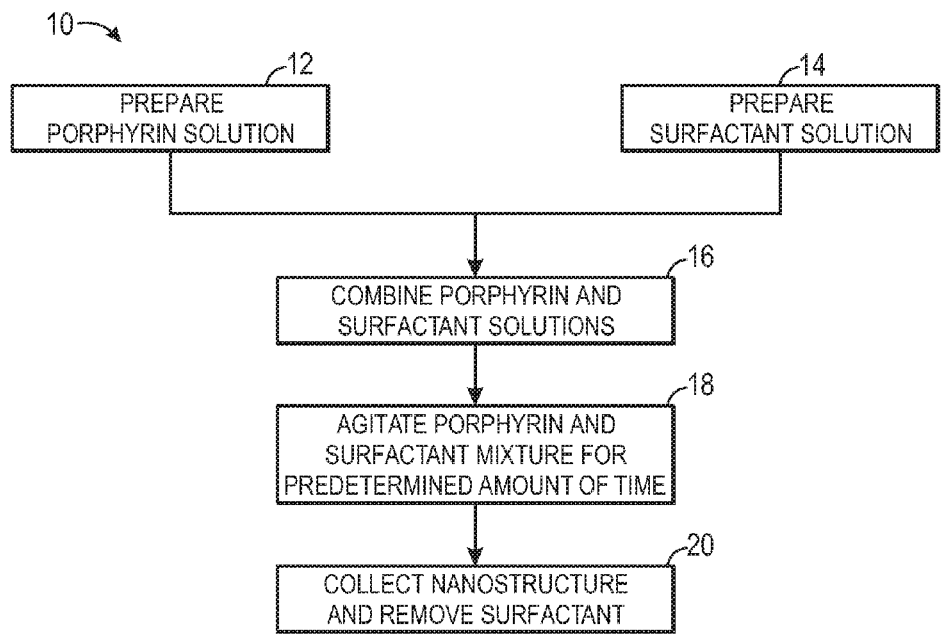
FIG. 1 is a flow chart illustrating an embodiment of a method for producing porphyrin nanostructures using a surfactant, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As noted above, in traditional methods for forming nanostructures, it can be difficult to predict and control the structure that is formed from a self-assembly process. This may be at least partially due to the lack of control of the way in which single molecules interact with each other, such as the lack of control over the extent to which molecules may agglomerate in a given solution. For one class of molecules, porphyrins, such a lack of control may be exacerbated by an increased variety of interactions, such as acid-base interactions, metal-ligand interactions, and so on.

Porphyrin molecules are particularly useful in that they exhibit a wide range of properties. As an example, heme, the naturally-occurring porphyrin in human blood, is responsible for carrying oxygen ($O_2$) though the body and removing carbon dioxide ($CO_2$) from tissues. In this way, it is believed that porphyrin nanostructures may therefore be useful for gas storage, as some gases may be retained at least by the metal to which the porphyrin is coordinated. Moreover, porphyrins contain a highly conjugated inner core, which allows them to have useful optical properties, such as photovoltaic behavior, phospholuminescence, and the like. In view of these properties, it may be desirable to produce porphyrin nanostructures for these and other uses. However, it is now recognized that traditional self-assembly techniques for producing porphyrin nanostructures lack the ability to control their dimensionality, morphology, and polydispersity, to name a few. Embodiments in accordance with the present disclosure address these and other shortcomings of traditional self-assembly methods by performing a surfactant-confined self-assembly reaction to control dimensionality, morphology, polydispersity, and physical properties of generated porphyrin nanostructures.

The surfactant-confined self-assembly methods described herein may generally take advantage of micellar formation by surfactants. Surfactants generally include a hydrophobic, or water-hating portion, and a hydrophilic, or water-loving portion. When placed into an aqueous solution, the surfactant molecules form sphere-like structures called micelles by packing the hydrophobic portions of the surfactant molecules together, such as towards a core of the sphere so as to avoid the aqueous solution. The hydrophilic portion of the surfactant is exposed to the surrounding solution, such as at the surface of the sphere. While not wishing to be bound by theory, it is believed that the self-assembly reactions described herein occur within such micelles, wherein single porphyrin molecules agglomerate inside the micelles and begin to self-assemble using van der Waals forces, π-π stacking, metal coordination, and other interactions.

With the foregoing in mind, a general description of methods for producing porphyrin nanostructures and example embodiments of the methods are provided hereinbelow. Specifically, FIG. 1 provides a general method for producing porphyrin nanostructures using a surfactant in a self-assembly reaction. As noted above, the general method set forth in FIG. 1 may be carried out at different levels of basicity or acidity, which can lead to different porphyrin nanostructures. Such methods are discussed with respect to FIGS. 4 and 27, respectively. In addition to varying the pH level of the reaction, other manipulations of the self-assembly reaction conditions such as the type and concentration of porphyrin, type and concentration of surfactant, and the order of adding the reagents may affect the morphology and size of the nanostructure produced by the disclosed methods. Such embodiments are described in the context of flowcharts and specific examples as they relate to the methods set forth in FIGS. 4 and 27 (i.e., in the context of a basic or acidic solution). Moreover, it should be noted that Examples 1-12 are actual examples of their respective methods.

Moving now to the figures and referring initially to FIG. 1, a method 10 is provided for producing porphyrin nanostructures by performing a surfactant-confined self-assembly reaction of porphyrin molecules. Prior to performing the self-assembly reaction, a porphyrin solution is prepared, as represented by a block 12, and a surfactant solution is prepared, as represented by a block 14. The porphyrin solution generally includes porphyrin molecules in an aqueous solution. The solvent that is used to disperse and/or dissolve the porphyrin may be water or any similar solvent that does not disturb micelle formation by the surfactant that is used.

Figure 2A:
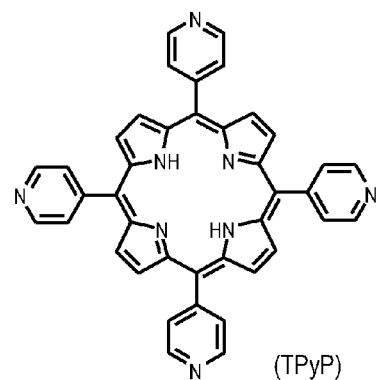
FIGS. 2a-2s are illustrations of non-limiting examples of porphyrins that may be used in the methods described in the present disclosure.
Figure 2B:
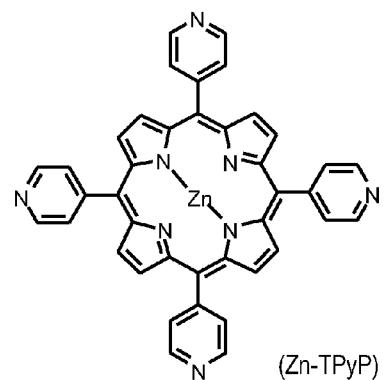
Figure 2C:
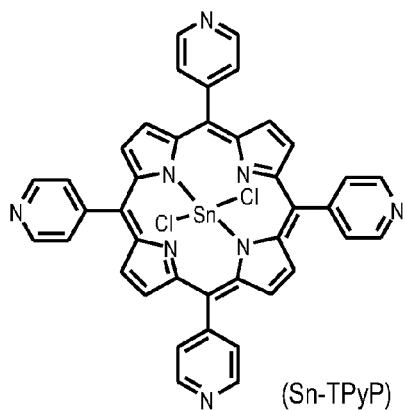
Figure 2D:
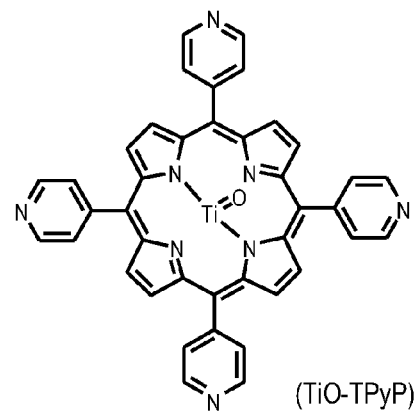
Figure 2E:
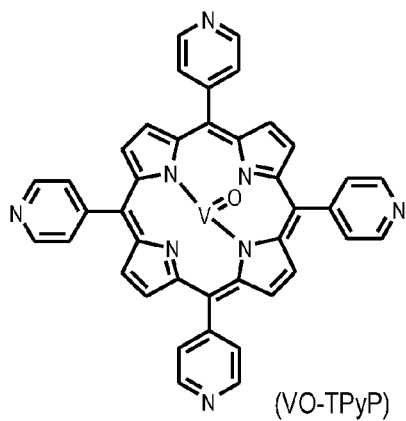
Figure 2F:
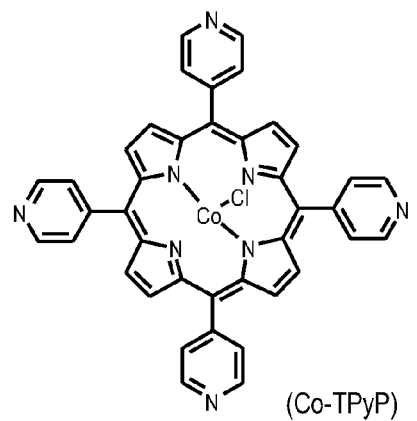
Figure 2G:
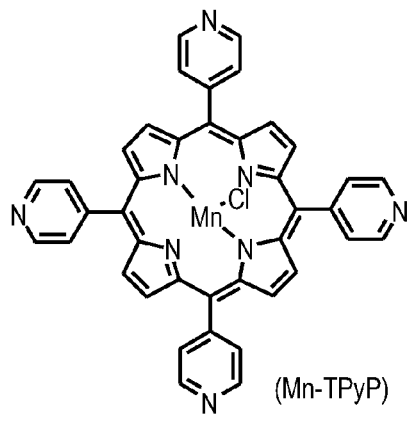
Figure 2H:
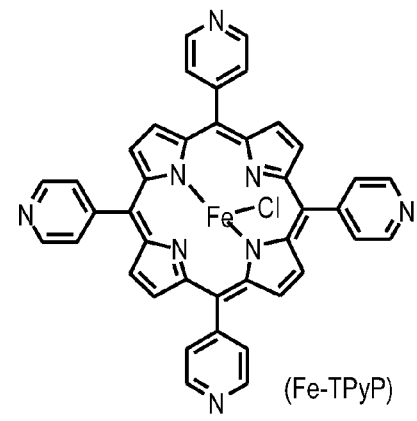

The porphyrin molecules in the porphyrin solution can have a variety of functionalities or moieties, such as chelating groups, chelated metals, solubilizing groups, chemical handles, and so on. Non-limiting examples of porphyrin molecules that may be used in accordance with the present disclosure include porphyrins having a porphine inner core and at least two pendant metal-coordinating (chelating) moieties. Non-limiting examples in accordance with the present disclosure include 5,10,15,20-tetra (4-pyridyl)-21H,23H-porphine (TPyP), zinc 5,10,15,20 tetra (4-pyridyl)-porphine (Zn-TPyP), tin (IV) meso-tetra (4-pyridyl) porphine dichloride (Sn-TPyP), titanium oxide meso-tetra (4-pyridyl) porphine (TiO-TPyP), vanadium oxide meso-tetra (4-pyridyl) porphine (VO-TPyP), cobalt (III) meso-tetra (4-pyridyl) porphine chloride (Co-TPyP), manganese (III) meso-tetra (4-pyridyl) porphine chloride (MnTPyP), iron(III) meso-tetra (4-pyridyl) porphine chloride (Fe(III)-TPyP), nickel (II) meso-tetra (4-pyridyl) porphine (Ni-TPyP), tetra (4-carboxyphenyl) porphine (TCP), copper (II) meso-tetra (4-carboxyphenyl) porphine (Cu-TCP), palladium (II) meso-tetra (4-carboxyphenyl) porphine (Pd-TCP), iron (III) meso-tetra (4-carboxyphenyl) porphine chloride (Fe(III)-TCP), iron (III) meso-tetra (4-sulfonatophenyl) porphine chloride (acid form) (Fe(III)-TSP), 5,10,15,20-tetrakis (4-hydroxyphenyl)-21H,23H-porphine (THP), 5,15-di(4-pyridyl)-10,20-diphenylporphyrin (DPyDPP), zinc (II) meso-trans-di(4-pyridyl) diphenyl porphine (Zn-DPyDPP), zinc (II) meso-tetra (2-pyridyl) porphine (Zn-T2PyP), and zinc (II) meso-tetra (3-pyridyl) porphine (Zn-T3PyP), the molecular structures of which are provided in FIGS. 2a-2s.

The porphyrin solution may be acidic, basic, or neutral depending on the aqueous solubility of the porphyrin to be used. That is, the pH of the porphyrin solution may range between about 2 to about 14. As an example, a porphyrin with basic groups, such as pyridyl moieties, may be prepared in an acidic solution. In this situation, the acid may protonate one or more of the pyridyl moieties to generate a mono- or multi-pyridinium species, which may have higher solubility in water compared to its non-protonated analog. Conversely, in situations where a porphyrin having acidic groups is used, such as a carboxylic acid-containing porphyrin, the solution may be basic. Of course, the base may deprotonate the carboxylic acid to generate a carboxy anion, which may have higher solubility in water than its protonated analog. In situations where the porphyrin is soluble in water, such as if the porphyrin contains solubilizing groups (e.g., poly(ethylene glycol) pendant groups), the porphyrin solution may be at a substantially neutral pH. The porphyrin solution may be prepared at any concentration, though it should be noted that the concentration of porphyrin may effect the amount of porphyrin solution that is ultimately used in the self-assembly reaction. In certain embodiments, such as in the examples provided below, the porphyrin may have a concentration of between about 0.005 moles/Liter (M) (5 mM) and about 0.020 M (20 mM). However, it should be understood that the concentration that is used may depend on the scale of the self-assembly reaction.

Figure 3A:
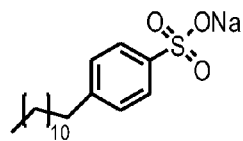
FIGS. 3a-3v are illustrations of non-limiting examples of surfactants that may be used in the methods described in the present disclosure.
Figure 3B:
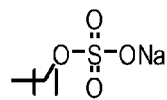
Figure 3C:
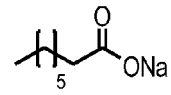
Figure 3D:
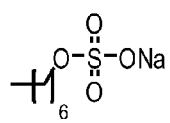
Figure 3E:
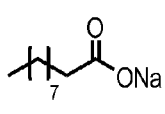
Figure 3F:
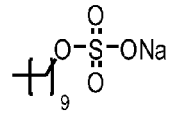
Figure 3G:
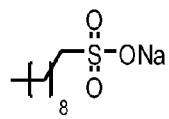
Figure 3H:
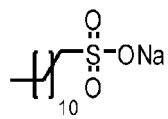
Figure 3I:
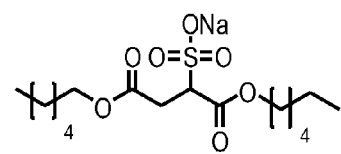
Figure 3J:
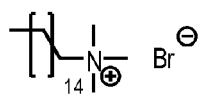
Figure 3K:
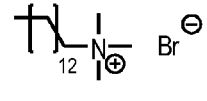
Figure 3L:
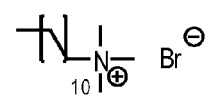
Figure 3M:
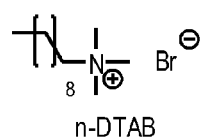
Figure 3N:
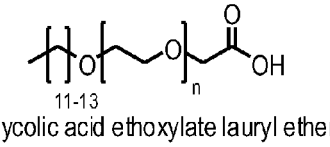
Figure 3O:
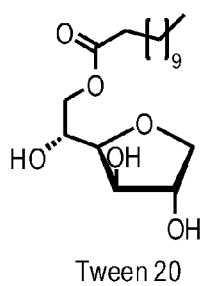
Figure 3P:
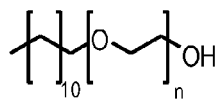
Figure 3Q:
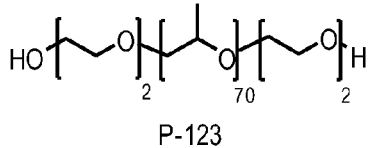
Figure 3R:
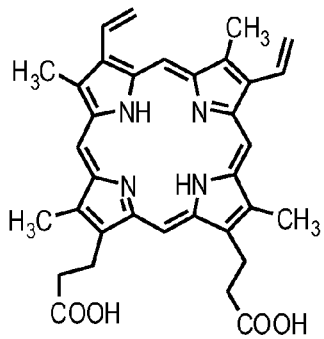
Figure 3S:
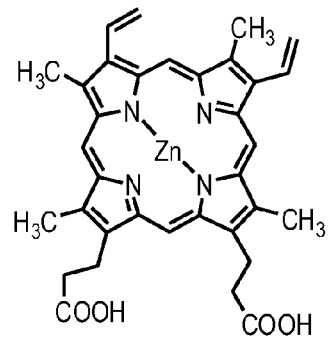
Figure 3T:
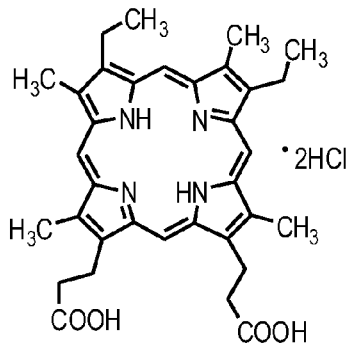
Figure 3U:
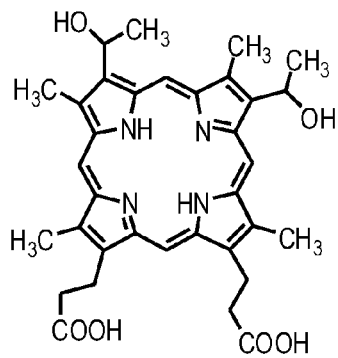
Figure 3V:
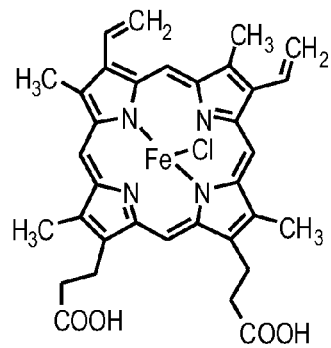

As noted above, in addition to the porphyrin solution, the surfactant solution is prepared prior to performing the self-assembly reaction. The surfactant solution generally includes a surfactant in an aqueous solution. The surfactant that is used in accordance with the present disclosure can be cationic, non-ionic, anionic, amphoteric, amphiphilic, and/or polymeric, to name a few. Non-limiting examples of the surfactant that may be used in the methods disclosed herein are provided in Table 1 below, along with their respective critical micelle concentrations (CMC). The molecular structures of the examples are provided in FIGS. 3a-3v.

TABLE 1

| Surfactant Type | Name | Abbreviation | Critical Micelle Concentration (CMC) |
|---|---|---|---|
| Ion Surfactant | sodium dodecyl benzene sulfonate | SDBS | 2.81 mM |
| | sodium dodecyl sulfate | SDS | 8.2 mM |
| | sodium octanoate | $C_7CO_2Na$ | 35.2 mM |
| | sodium octylsulfate | $C_8SO_4Na$ | 132 mM |
| | sodium decanoate | $C_9CO_2Na$ | 116 mM |
| | sodium decyl sulfate | $C_{10}SO_4Na$ | 28 mM |
| | sodium 1-decanesulfonate | $C_{10}SO_3Na$ | 40.6 mM |
| | sodium 1-dodecanesulfonate | $C_{12}SO_3Na$ | 9.8 mM |
| | docusate sodium | | 0.45 mM |

TABLE 1-continued

| Surfactant Type | Name | Abbreviation | Critical Micelle Concentration (CMC) |
|---|---|---|---|
| Cation Surfactant | cetyl trimethylammonium bromide (CTAB) | CTAB ($C_{16}$) | 0.80 mM |
| | trimethyl(tetradecyl) ammonium bromide (MTAB) | MTAB ($C_{14}$) | 3.5 mM |
| | dodecyl trimethyl ammonium bromide | DTAB ($C_{12}$) | 14.1 mM |
| | n-decyltrimethylammonium bromide | N-DTAB ($C_{10}$) | 61 mM |
| Nonionic surfactant | glycolic acid ethoxylate lauryl ether | | No report for CMC |
| | Tween 20 | | 0.08 mM |
| | Brij@35 | | 0.09 mM |
| | Poly(ethylene glycol)-block-poly(propylene glycol)-block-poly(ethylene glycol) | P-123 MW:5800 | 0.4 g/L |
| Amphilic Porphyrin Surfactant | Protoporphyrin IX zinc(II) | | No report for CMC |
| | Protoporphyrin IX | | |
| | Hematoporphyrin IX dihydrochloride | H678 | |
| | Hematoporphyrin: 8,13-Bis(1-hydroxyethyl)-3,7,12,17-tetramethyl-21H,23H-porphine-2, 18-dipropionic acid | | |
| | Heroin Ferriprotoporphyrin IX chloride | | |

The amount of surfactant in the surfactant solution, represented as the surfactant concentration, may depend on the type of surfactant used as well as the desired morphology and size of the porphyrin nanostructure produced by the self-assembly reaction. Moreover, in accordance with the present disclosure, the surfactant may have a concentration that is approximately at or above its critical micelle concentration (CMC), which is the approximate minimum concentration suitable for a given surfactant to form a micelle. Thus, each surfactant has a unique CMC, as shown in Table 1 above. However, it should be noted that concentrations of surfactant below its CMC may also be suitable for the self-assembly reaction, depending on the desired characteristics of a given nanostructure product. In certain embodiments, such as in the examples provided below, the surfactant solution may have a concentration between about 0.0005 M (0.5 mM) and 0.020 M (20 mM). As noted above with respect to the porphyrin solution, however, it should be understood that the concentration that is used may depend on the scale of the self-assembly reaction. The solvent of the surfactant solution may be any solvent in which micelles may be formed by the surfactant, such as water. However, it should be noted that studies performed using SDS as the surfactant in solvents other than water, such as alkanol solvents (i.e., methanol, ethanol, etc.) resulted in ill-defined nanostructures. Indeed, in such solvents, micelle formation may not be favorable. However, it should be noted that the use of any combination of solvent and surfactant is contemplated herein as long as the micelles formed by the surfactant are not disrupted.

The surfactant solution may be at a pH that is at least partially determined by the pH of the porphyrin solution and the type of surfactant to be used. Indeed, the pH of the surfactant solution may have a similar range to that of the porphyrin solution, which may range between about 2 to about 14. As an example, in embodiments where the porphyrin solution is acidic, the surfactant solution may be basic, and in embodiments where the porphyrin solution is basic, the surfactant solution may be acidic. However, it should be noted that in some situations the porphyrin solution and the surfactant solution may both be acidic or may both be basic.

Once the porphyrin and surfactant solutions have been prepared as represented by blocks 12 and 14, the solutions may be combined, which is represented at block 16. The act of combining the solutions may include combining the solutions substantially all at once, or may include adding one solution to the other. For example, the porphyrin solution may be added to the surfactant solution either slowly or all at once, or the surfactant solution may be added to the porphyrin solution either slowly or all at once. As noted above, the ultimate concentration of the porphyrin and the surfactant may be a factor that contributes to the size and/or morphology of a resulting nanostructure. Moreover, the ratio in which the porphyrin and surfactant are present may also affect the efficiency of the reaction and the degree of dispersity of the resulting nanostructures. In accordance with the present disclosure, the molar ratio of surfactant to porphyrin may range between about 2:1 to about 40:1, such as about 4:1, 5:1, 10:1, 20:1, 30:1, or 40:1. However, it should be noted that at ratios below about 3:1, the plurality of nanostructures that are formed may not be monodisperse in any dimension, such as length, diameter, edge length, and so on. Further, in embodiments where the concentration of porphyrin solution and the concentration of surfactant in the surfactant solution are substantially the same, the molar ratio may also be approximately equal to the volume ratio that is used when the solutions are combined.

Once the porphyrin and surfactant solutions have been combined, they are agitated, as represented by a block 18. The agitation may include stirring, shaking, sonication, convection, and so on. The agitation may be performed at any suitable temperature, such as low temperatures (e.g., between about 0° C. and 20° C.), at room temperature (e.g., between about 20° C. and 30° C.), or with heating (e.g., between about 30° C. and 100° C.). Moreover, the agitation may be performed for a predetermined amount of time, such as between two minutes and two days (e.g., 1 hour, 24 hours, 48 hours), or the agitation may be performed until a desired nanostructure morphology and size has been obtained. For example, the mixture may be agitated and then sampled at predetermined time intervals to ascertain the status of any nanostructures that may be present. The nanostructures may be monitored by spectroscopic methods such as UV/Vis, fluorescence, nuclear magnetic resonance (NMR) and/or by imaging methods such as AFM, SEM, fluorescence microscopy, scanning tunneling microscopy (STM), transmission electron microscopy (TEM), or any similar microscopy technique with sufficient resolution to ascertain nanostructure profiles. When the desired nanostructure is obtained and/or the predetermined amount of time has lapsed (i.e., the self-assembly reaction is complete), the agitation is stopped.

After completion of the self-assembly reaction, the nanostructure is collected by separating the surfactant from the formed nanostructures, as represented by a block 20. For example, the mixture containing at least the nanostructures and the surfactant may be diluted to where the concentration of the surfactant is sufficiently below its CMC that substantially all of the surfactant micelles are destroyed. The mixture may then be filtered, for example using a micro and/or nanopore filter. Alternatively or additionally, in one embodiment, the mixture may by centrifuged using a given rotation speed (e.g., 5000 rpm, 6000 rpm, 7000 rpm or more). The supernatant may then be discarded and the remaining precipitate (nanostructures) washed with fresh solvent (e.g., water). The washing/centrifuging process may be performed until the nanostructures are substantially free of surfactant.

Figure 4:
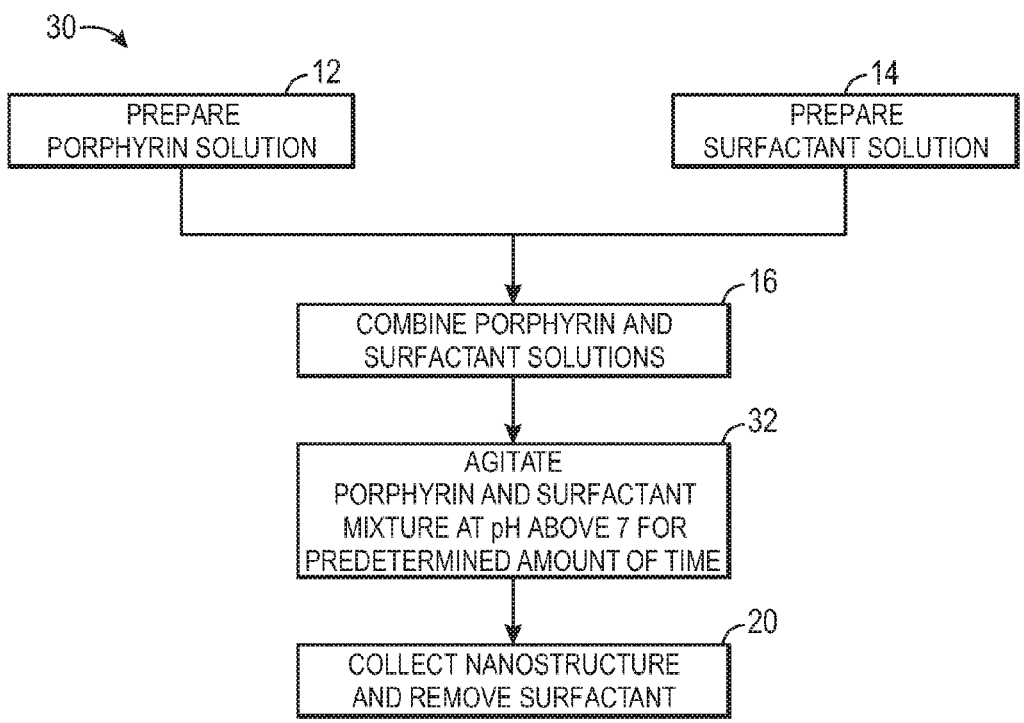
FIG. 4 is a flow chart illustrating an embodiment of the method for producing porphyrin nanostructures of FIG. 1 wherein the porphyrin-surfactant mixture is maintained at a pH above 7, in accordance with aspects of the present disclosure.

As noted above, the methods disclosed herein to produce porphyrin nanostructures via surfactant-confined self-assembly may be performed at a variety of pH levels. FIG. 4 provides one such method 30 for producing porphyrin nanostructures at pH levels above about 7 (i.e., under basic conditions). In a general sense, performing the surfactant-confined self-assembly at pH levels above about 7 may produce porphyrin nanostructures having aspect ratios above unity, such as nanorods, nanowires, and the like. However, the pH of the solution may not be the only factor leading to nanostructure morphology. For example, the particular porphyrin and/or surfactant that are used may affect the resulting nanostructure. In one embodiment, using a porphyrin having a 4-pyridine chelating functionality, such as Zn-TPyP, may result in a nanorod or nanowire. However, when the porphyrin is changed from having a 4-pyridyl chelating functionality to a 2-pyridyl chelating functionality, the resulting nanostructure may be a 2D nanosheet rather than a 1D nanorod. In this way, the nanostructures formed in accordance with the present embodiments may depend on several factors, as described above. Accordingly, several experimental examples of method 30 are provided below.

In a similar manner to the method 10 described above with respect to FIG. 1, to begin the method 30, the acts represented by blocks 12 and 14 are performed prior to running the self-assembly reaction. After the porphyrin and surfactant solutions have been prepared, they are combined as described above with respect to block 16. Once the solutions have been combined, they are agitated at a pH above about 7, such as at a pH of about 7.5, 8, 9, 10, 11, 12, 13, or 14, as represented by a block 32.

The pH of the agitated mixture may be brought above 7 by controlling the pH of the porphyrin and surfactant solutions prior to combining at block 16, or may be brought above 7 after the solutions are combined at block 16. Examples relating to the former method are provided herein below, and examples relating to the latter method are provided with respect to the method set forth in FIG. 21. As an example of pH control prior to mixing, the porphyrin solution may be prepared at a pH of about 2, and the surfactant solution may be prepared at a pH of about 14. Depending on the ratio of surfactant solution to porphyrin solution, the pH of the resulting mixture may be between about 8 and 12. Upon agitating the mixture for a predetermined amount of time, as described above, the porphyrin nanostructures are collected by removal of at least a portion of the surfactant, as represented by block 20. One embodiment of the method 30 is provided below in Example 1, which is an actual example wherein ZnTPyP is self-assembled in the presence of SDS surfactant at a pH of 11.5. In the examples provided herein, it should be noted that all porphyrin molecules were purchased from Frontier Scientific and used without further purification. The surfactants used were purchased form Sigma Aldrich and used without further purification.

Example 1

A 0.5 ml of stock ZnTPyP solution (fresh) in water (0.01 M, 0.2 M HCl) was added into 9.5 ml of SDS solution (0.01 M, containing 0.2 mmol NaOH), resulting in a mixture at a pH of 11.5. The mixture was continuously stirred for 48 h at room temperature (about 25° C.). The resulting green solution was then centrifuged at 7000 rpm for 20 min and washed twice with Millipore™ water to remove the SDS surfactant. A representative SEM image of the plurality of hexagonal porphyrin nanorods produced by the self-assembly reaction is provided in FIG. 5.

Figure 5:
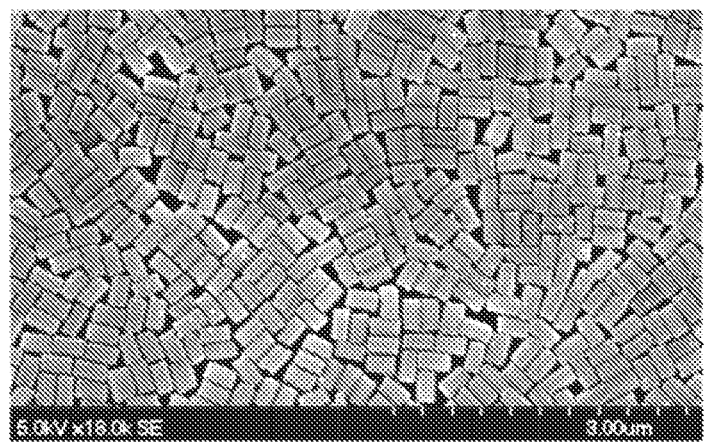
FIG. 5 is a scanning electron microscopy (SEM) image of a plurality of hexagonal nanorods produced using an embodiment of the method set forth in FIG. 4, in accordance with an aspect of the present disclosure.
Figure 6:
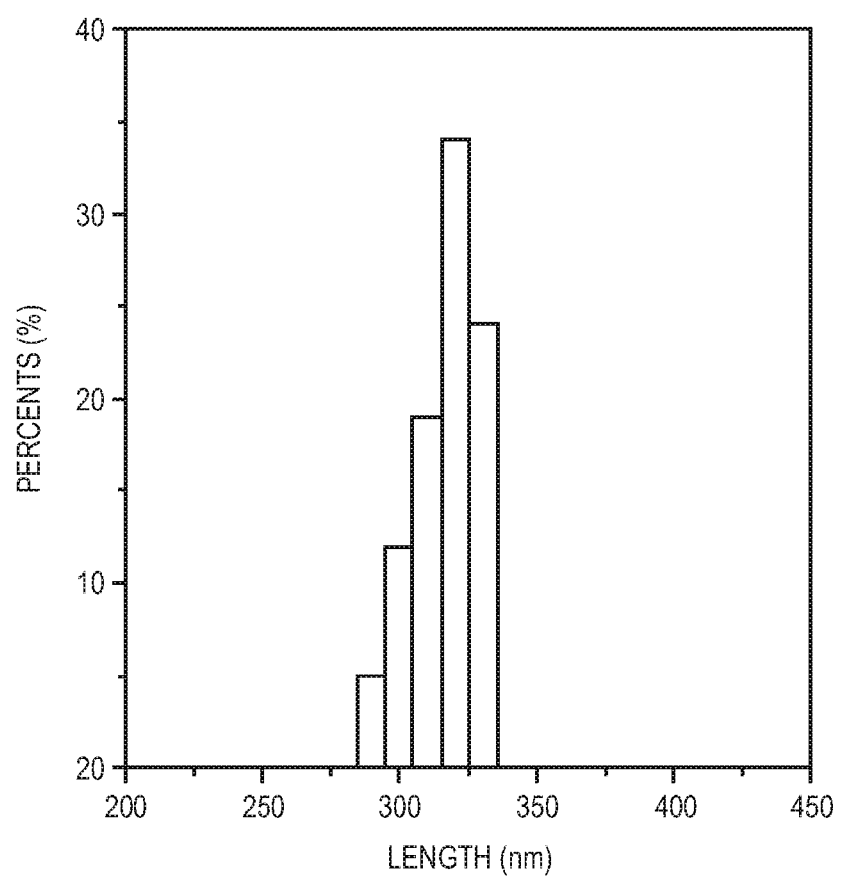
FIG. 6 is a population histogram of the lengths of the plurality of nanorods in the image of FIG. 5, in accordance with an aspect of the present disclosure.

Specifically, FIG. 5 is a top-down view of the hexagonal porphyrin nanorods, wherein substantially all (nearly 100%) of the nanorods have a length of about 320±20 nm, as represented in the population histogram of FIG. 6. Indeed, as shown in FIG. 6, approximately 90% of the hexagonal porphyrin nanorods have a length of between about 300 nm and 330 nm. According to the present disclosure, such a plurality of hexagonal porphyrin nanorods may be considered monodisperse in the length dimension.

Figure 7:
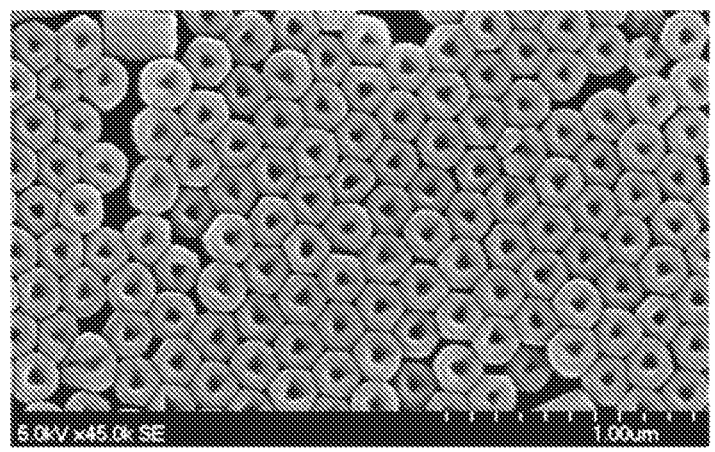
FIG. 7 is an SEM image of the plurality of hexagonal nanorods of FIG. 5 produced using an embodiment of the method set forth in FIG. 4, in accordance with an aspect of the present disclosure.
Figure 8:
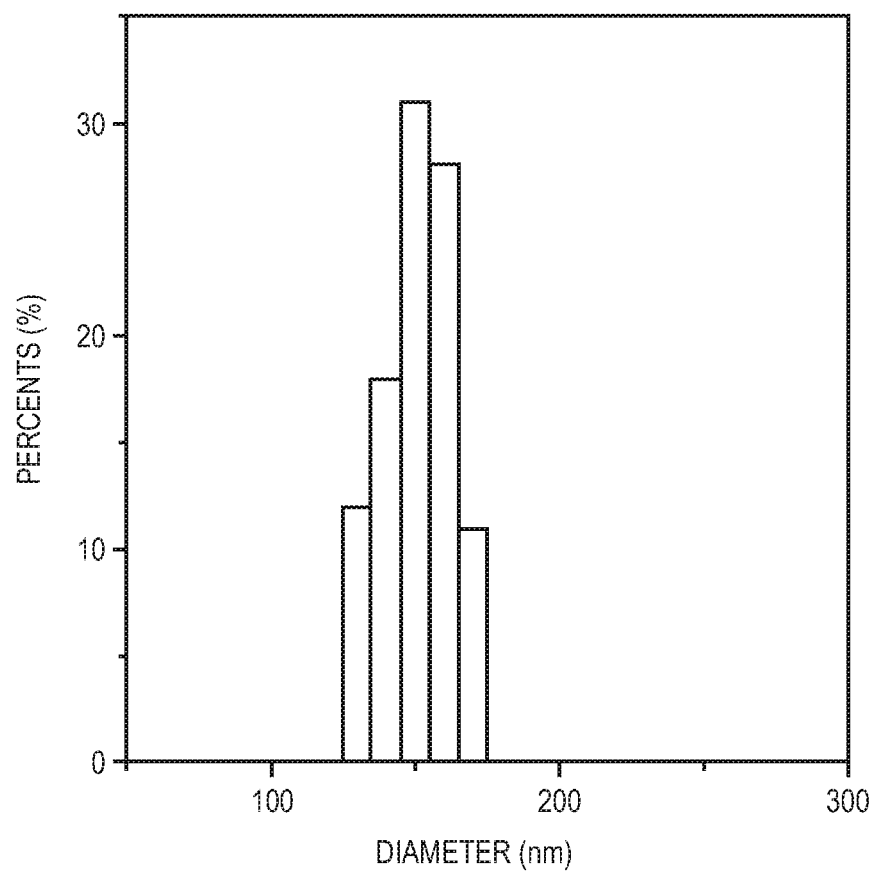
FIG. 8 is a population histogram of the diameters of the plurality of nanorods in the images of FIGS. 5 and 7, in accordance with an aspect of the present disclosure.

In addition to monodispersity in their length dimension, the hexagonal porphyrin nanorods may also have similar characteristics with regard to their diameters. The diametrical extents as well as the shape of the hexagonal porphyrin nanorods may be further appreciated with respect to FIG. 7, which is an SEM image of the hexagonal porphyrin nanorods imaged end-on. It may be noted upon viewing the image of FIG. 7 that the plurality of hexagonal porphyrin nanorods appear to have similar diameters. Indeed, as shown in FIG. 8, which illustrates the population distribution of the diameters of the hexagonal porphyrin nanorods of FIG. 7, substantially all (about 100%) of the hexagonal porphyrin nanorods have a diameter of about 150±15 nm. According to the present disclosure, such a plurality of hexagonal porphyrin nanorods may be considered monodisperse in the diameter dimension.

Figure 9:
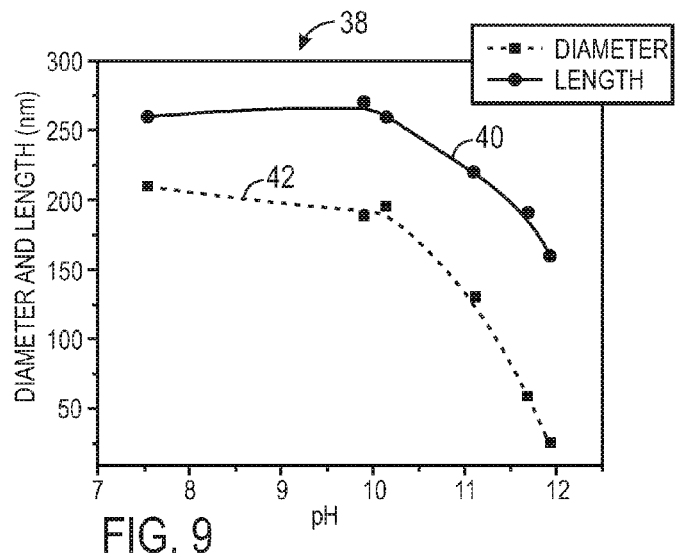
FIG. 9 is a plot of hexagonal nanorod diameter and length as a function of the pH used in an embodiment of the method of FIG. 4, in accordance with an aspect of the present disclosure.
Figure 10:
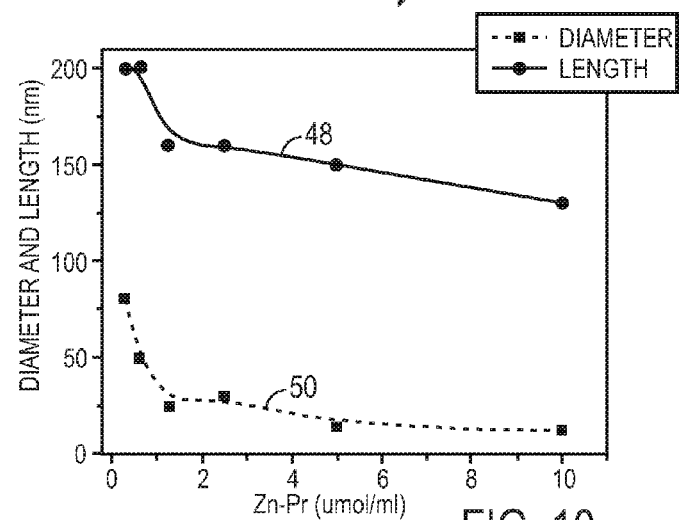
FIG. 10 is a plot of hexagonal nanorod diameter and length as a function of the concentration of porphyrin used in an embodiment of the method of FIG. 4, in accordance with an aspect of the present disclosure.
Figure 11:
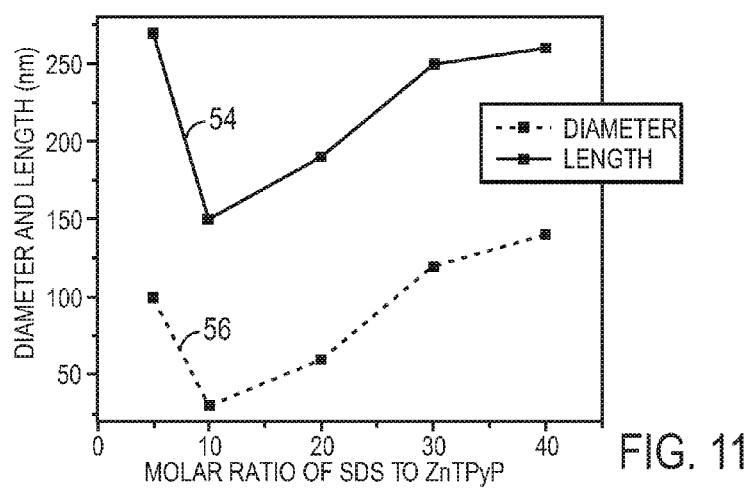
FIG. 11 is a plot of hexagonal nanorod diameter and length as a function of the molar ratio of surfactant to porphyrin used in an embodiment of the method of FIG. 4, in accordance with an aspect of the present disclosure.

In regards to the method 30 utilized to produce the hexagonal porphyrin nanorods in Example 1, the length and diameter dimensions of the hexagonal porphyrin nanorods produced using SDS as the surfactant and Zn-TPyP as the porphyrin may be manipulated by changing the conditions of the self-assembly reaction. For example, as noted above, the pH may be manipulated (i.e., between 7 and 14), and the concentrations of the porphyrin and/or surfactant in the reaction mixture may be manipulated. Such variations in the reaction conditions of Example 1 and their effect on the hexagonal porphyrin nanorods so produced are represented by FIGS. 9-11, which show the average diameter and lengths of the hexagonal porphyrin nanorods as a function of pH, Zn-TPyP concentration, and molar ratio of SDS to Zn-TPyP, respectively. It should be noted that similar relationships may exist for other porphyrin nanostructures discussed herein.

As noted above, FIG. 9 illustrates a plot 38 of the diameters and lengths of the hexagonal porphyrin nanorods. In a general sense, the dimensions of the hexagonal porphyrin nanorods may decrease with increasing pH. Specifically, line 40 represents the average length of the hexagonal porphyrin nanorods as a function of pH, and line 42 represents the average diameter of the hexagonal porphyrin nanorods as a function of pH. With regard to line 40, the average lengths of the hexagonal porphyrin nanorods remain substantially the same (between about 260 nm and about 270 nm) from a pH of about 7.5 to a pH of about 10. However, as the pH increases above about 10, the average lengths of the hexagonal porphyrin nanorods begin to decrease. As illustrated, the average lengths of the hexagonal porphyrin nanorods decrease to about 225 nm at a pH of about 11.1, about 200 nm at a pH of about 11.6, and about 160 nm at a pH of about 12. Similarly, line 42 remains substantially the same at about 210 nm to about 200 nm between a pH of about 7.5 to a pH of about 10.1. At a pH above about 10.1, the average diameters of the hexagonal porphyrin nanorods decrease precipitously. For example, the average diameters are about 135 nm at a pH of about 11.1, about 60 nm at a pH of about 11.6, and about 25 nm at a pH of about 12.

As noted above, the effect of porphyrin concentration also affects the resulting diameters and lengths of nanostructures produced in accordance with the present methods. Indeed, the hexagonal porphyrin nanorods that are produced using conditions similar to those in Example 1 at a pH between about 11.7 and about 11.9 experience changing diameters and lengths as the concentration of the porphyrin is varied. FIG. 10 is a plot 46 of such relationships. Specifically, the plot 46 includes a line 48 representative of the average lengths and a line 50 representative of the average diameters of the hexagonal porphyrin nanorods as a function of changing porphyrin (Zn-TPyP) concentration.

In plot 46, as the concentration of the porphyrin increases, the diameter and length decrease. For example, between concentrations of about 0.1 mM and 1 mM, the diameter and lengths of the hexagonal porphyrin nanorods decrease as the concentration is increased. However, once the concentration is above about 1 mM, the average lengths and diameters of the hexagonal porphyrin nanorods remain about the same. For example, at concentrations above about 1 mM, the average diameters of the hexagonal porphyrin nanorods remain between about 10 nm and 25 nm, and the average lengths of the hexagonal porphyrin nanorods remain between about 160 nm and 130 nm.

FIG. 11 is a plot 52 of the relationship between the average lengths and diameters of the hexagonal porphyrin nanorods produced in accordance with the reaction conditions of Example 1, with varying surfactant-to-porphyrin ratio. Specifically, a line 54 represents the average lengths and a line 56 represents the average diameters of hexagonal porphyrin nanorods produced as a function of the molar ratio of SDS to Zn-TPyP. Generally, the average lengths and diameters of the hexagonal porphyrin nanorods decrease from about 275 nm and about 100 nm, respectively, to about 150 nm and about 10 nm, respectively as the ratio of surfactant to porphyrin is increased from about 5 to about 10. However, at ratios above about 10, the average lengths and diameters of the hexagonal porphyrin nanorods increase.

In view of the foregoing trends exemplified with respect to FIGS. 9-11, it should be noted that the size of all of the nanostructures described herein may exhibit dependence on pH as well as surfactant and porphyrin concentrations. Indeed, at certain pH levels and surfactant/porphyrin concentrations, the nanostructures formed by the self-assembly method of FIG. 4 may produce other nanostructures, such as nanowires, rectangular nanorods, and others. Additionally, by changing the surfactant and/or porphyrin, other nanostructures may be produced. Non-limiting examples of such variations in surfactant are provided below in Examples 2 and 3. Specifically, similar conditions to those of Example 1 are used in the conditions of Example 2, but the surfactant is changed from an anionic surfactant, SDS, to a cationic surfactant, CTAB. A similar substitution is made in Example 3, wherein the surfactant is MTAB, another cationic surfactant.

Example 2

A 0.5 ml of stock Zn-TPyP solution in water (0.1 M, 0.2 M HCl) was added into 9.5 ml of a CTAB solution (0.01 M, containing 0.2 mmol NaOH) with continuous stirring. The resulting solution pH was 11.7. The mixture was stirred at room temperature (25° C.) for 48 h resulting in a green solution. The green solution was centrifuged at 7000 rpm for 20 min and washed twice with Millipore™ water to remove the surfactant. A representative SEM image of the plurality of long porphyrin nanowires produced by the self-assembly reaction is provided in FIG. 12.

Figure 12:
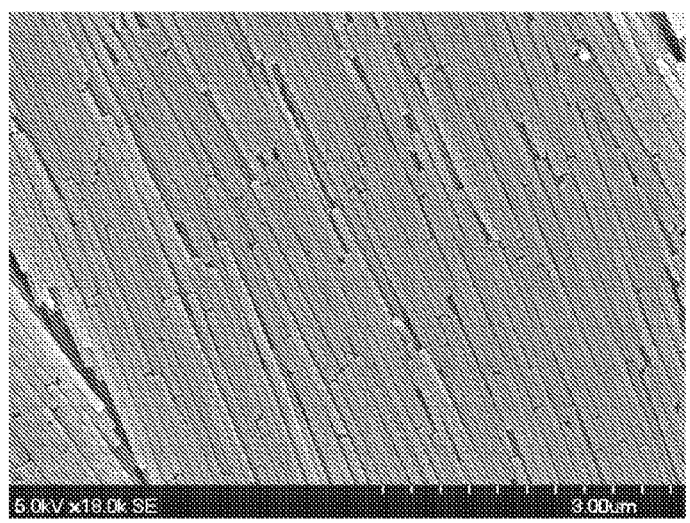
FIG. 12 is an SEM image of a plurality of long porphyrin nanowires produced using an embodiment of the method set forth in FIG. 4, in accordance with an aspect of the present disclosure.
Figure 13:
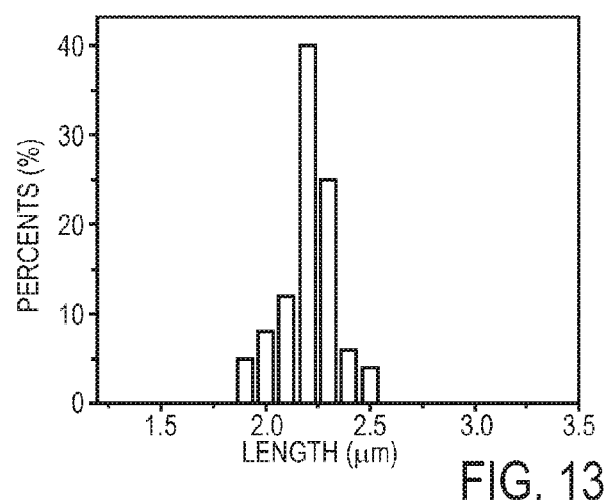
FIG. 13 is a population histogram of the lengths of the plurality of long porphyrin nanowires in the image of FIG. 12, in accordance with an aspect of the present disclosure.
Figure 14:
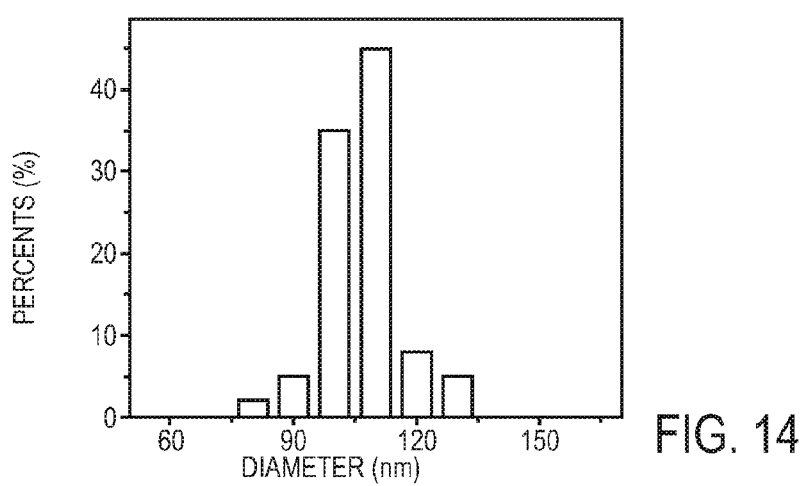
FIG. 14 is a population histogram of the diameters of the plurality of long porphyrin nanowires in the image of FIG. 12, in accordance with an aspect of the present disclosure.

Specifically, FIG. 12 is a top-down view of the long porphyrin nanowires, wherein substantially all (nearly 100%) of the nanorods have a length between about 2.2±0.18 μm, as represented in the population histogram of FIG. 13. FIG. 14 illustrates the population distribution of the diameters of the long porphyrin nanowires of FIG. 12. As represented by FIG. 14, substantially all (about 100%) of the long porphyrin nanowires have a diameter of about 105±8 nm. Indeed, over 80% of the long porphyrin nanowires produced in the conditions of Example 2 have a diameter of between about 100 and about 105 nm. According to the present disclosure, such a plurality of long porphyrin nanowires may be considered a monodisperse mixture.

Example 3

A 0.5 ml of stock Zn-TPyP solution (stored for longer than 48 h) in water (0.01 M, 0.2 M HCl) was added into 9.5 ml of an MTAB solution (0.01 M, containing 0.2 mmol NaOH). The resulting solution pH was 11.6. The mixture was stirred at room temperature (25° C.) for 48 h. The solution was then centrifuged at 8000 rpm for 30 min and washed twice with Millipore™ water to remove the surfactant. An SEM image of a plurality of rectangular porphyrin nanorods produced by the self-assembly reaction is provided in FIG. 15. The rectangular morphology of the rectangular porphyrin nanorods may be further appreciated with reference to FIG. 15a, which is an expanded view of a portion of the image of FIG. 15.

The plurality of rectangular porphyrin nanorods in FIG. 15 all have a length of about 290±20 nm, as represented in the population histogram of FIG. 16. Moreover, over 85% of the rectangular porphyrin nanorods have lengths of about 290±10 nm. FIG. 17 illustrates the population distribution of the diameters of the rectangular porphyrin nanorods of FIG. 15. As represented by FIG. 17, substantially all (about 100%) of the long porphyrin nanowires have a diameter of about 90±10 nm. According to the present disclosure, such a plurality of rectangular porphyrin nanorods may be considered a monodisperse mixture.

Figure 18:
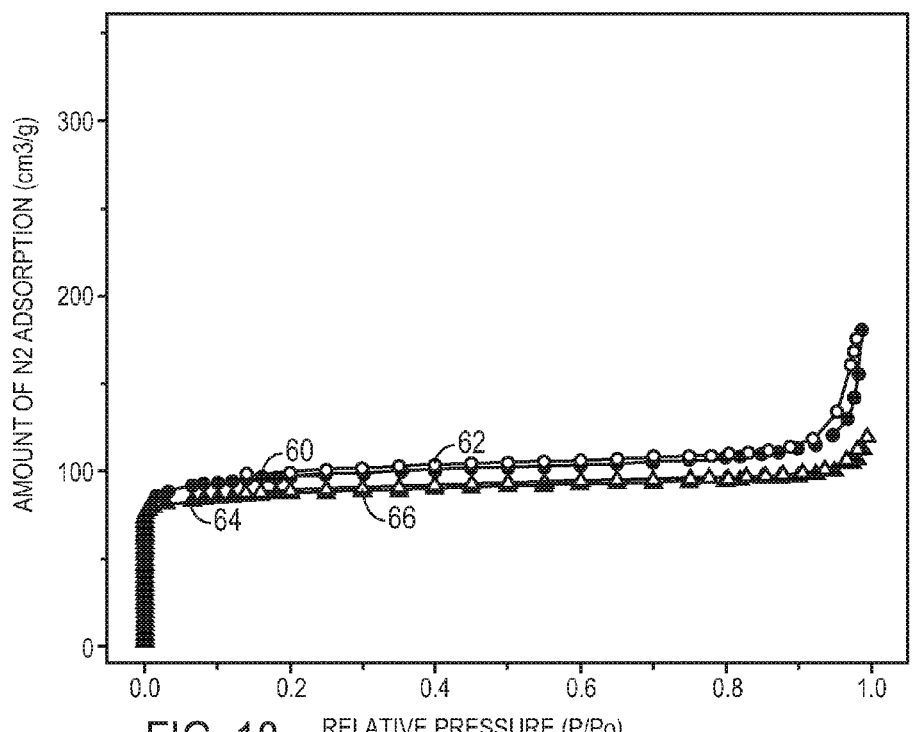
FIG. 18 is a plot of nitrogen absorption and desorption as a function of relative pressure for hexagonal porphyrin nanorods and long porphyrin nanowires produced using varying embodiments of the method of FIG. 4, in accordance with an aspect of the present disclosure.
Figure 19:
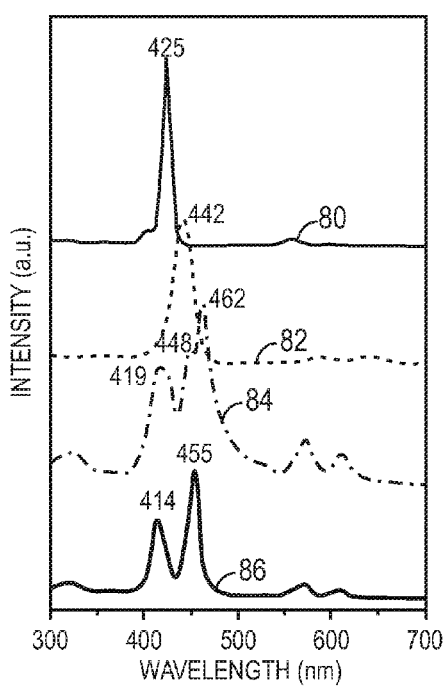
FIG. 19 is a combined ultraviolet/visible (UV/Vis) light absorbance spectrum comparing the absorbance of a non-self assembled porphyrin in a polar aprotic solvent, a non-self assembled porphyrin in an acidic aqueous solution, a solution of hexagonal porphyrin nanorods produced using an embodiment of the method of FIG. 4, and a solution of long porphyrin nanowires produced using an embodiment of the method of FIG. 4, in accordance with an aspect of the present disclosure.
Figure 20:
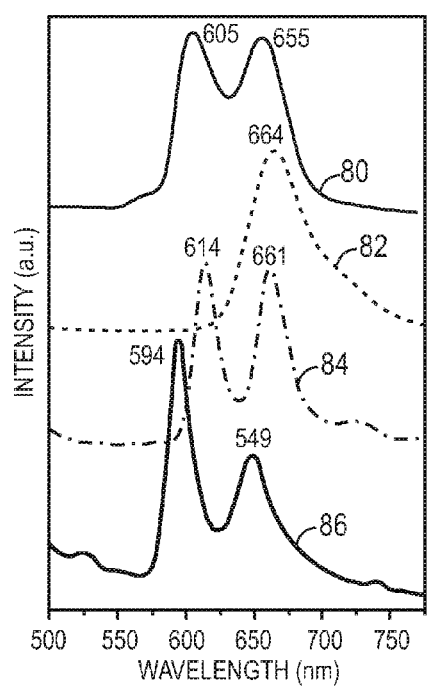
FIG. 20 is an expanded view of a portion of the combined spectrum of FIG. 19, in accordance with an aspect of the present disclosure.

The monodisperse mixtures of hexagonal porphyrin nanorods, long porphyrin nanowires, and rectangular porphyrin nanorods exhibit properties that may allow them to be used for a number of potential applications, such as gas (e.g., hydrogen) storage, photovoltaics, and so on. FIGS. 18-20 provide gas sorption and optical data for the hexagonal porphyrin nanorods and long porphyrin nanowires produced according to Examples 1 and 2.

Specifically, FIG. 18 provides nitrogen ($N_2$) sorption data for hexagonal porphyrin nanorods and long porphyrin nanowires. The $N_2$ sorption data was measured on a Micromeritics ASAP 2010 system. In a standard experiment, a powder of the nanostructure was placed into a glass container and sealed using Viton O-rings. The container was degassed for 24 h at 50° C. under vacuum. The $N_2$ sorption isotherms were then obtained at 77K.

In FIG. 18, a line 60 represents the $N_2$ adsorption of the hexagonal porphyrin nanorods while a line 62 represents their $N_2$ desorption. A line 64 represents the $N_2$ adsorption of the long porphyrin nanowires, and a line 66 represents their $N_2$ desorption. It should be noted that the hexagonal porphyrin nanorods and the long porphyrin nanowires are characteristic type I isotherms (according to IUPAC classification), which is indicative that the adsorbents (i.e., the nanostructures) are microporous. Adsorption and desorption traces of the nanostructures are substantially the same, which is indicative that the nanostructures do not exhibit any apparent hysteresis.

FIGS. 19 and 20 contain UV/Vis absorbance data for Zn-TPyP in a polar aprotic solvent dimethylformamide (DMF) as represented by a line 80, for Zn-TPyP in 1N HCl as represented by a line 82, for hexagonal porphyrin nanorods as represented by a line 84, and for long porphyrin nanowires as represented by a line 86. As the data suggests, the hexagonal porphyrin nanorods and the long porphyrin nanowires absorb in about the same regions. However, the hexagonal porphyrin nanorods and the long porphyrin nanowires exhibit at least two distinct maxima between about 410 nm and about 465 nm, compared to one maximum absorption peak for the single porphyrin molecules from which they are formed. While not wishing to be bound by theory, it is believed that such optical behavior may be the result of inter-coordination between multiple porphyrin molecules in the self-assembled nanostructures. As will be described further below, the optical behavior of the nanostructures generated using the methods described herein may exhibit dimension- and morphology-dependent optical behavior.

Figure 21:
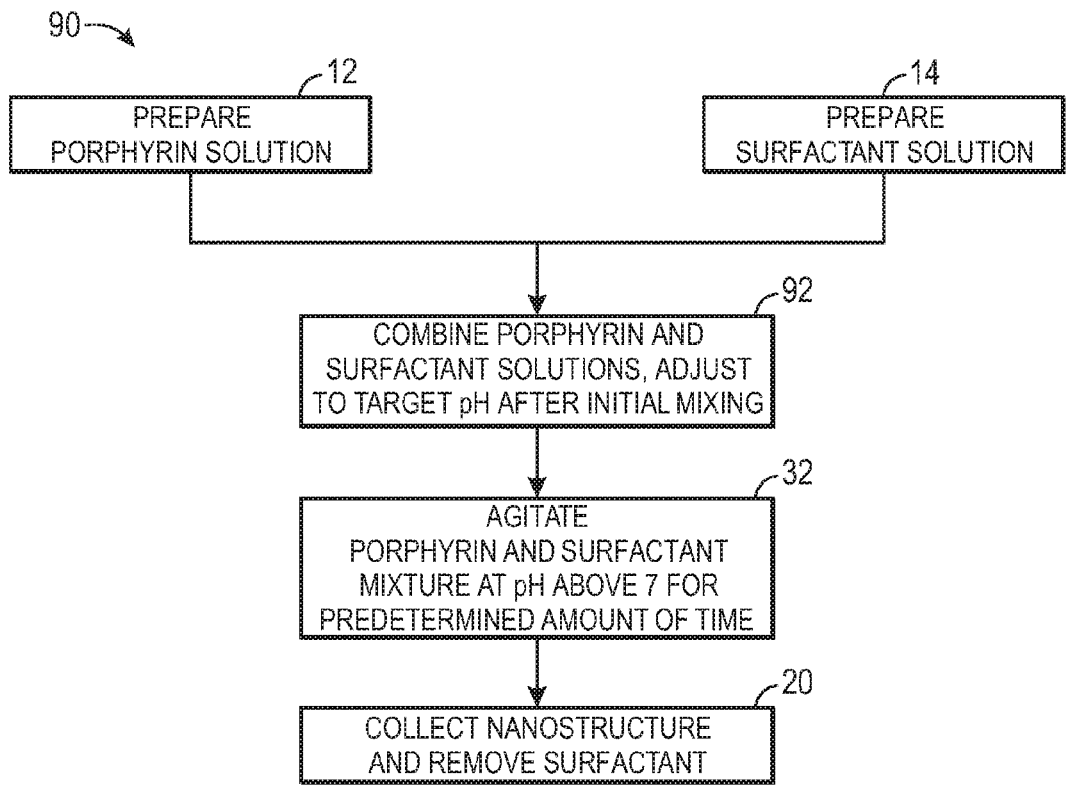
FIG. 21 is a flowchart illustrating an embodiment of the method of FIG. 4, wherein the pH of the mixture is adjusted after the porphyrin solution and the surfactant solution are combined, in accordance with an aspect of the present disclosure.

In accordance with another aspect of the present disclosure, the dimensions and morphology of nanostructures produced by the general method according to FIG. 1 may also depend, as noted above, on the order in which the reagents are added to the self-assembly reaction mixture. FIG. 21 illustrates a flow chart depicting an embodiment of a method 90 wherein the pH of the self-assembly reaction mixture is adjusted after the porprhyin solution and the surfactant solution have been prepared (i.e., the surfactant solution is neutral). Thus, the acts represented by blocks 12 and 14 are performed. However, the surfactant solution is maintained at a substantially neutral pH (i.e., no acid or base is added). Once the solutions have been prepared, the solutions are combined, and the pH of the combined mixture is then adjusted, as represented by a block 92. In the context of a basic reaction mixture, the pH would be adjusted to above 7 by adding base, such as a metal hydroxide (e.g., NaOH). The pH-adjusted solution is then agitated for a predetermined amount of time, as represented by block 32. The surfactant is thereafter removed and the nanostructures are collected.

It should be noted that by using reaction conditions nearly identical to those described above in Example 1, hexagonal porphyrin nanorods having larger average diameters and larger average lengths may be obtained. As another example, at a final self-assembly reaction pH of about 12.4, the average diameter and length of nanorods obtained by adjusting the pH after initial mixing is 75 nm and 800 nm, respectively, compared to a much smaller average diameter and length of 35 nm and 280 nm, respectively, for nanorods produced by pre-adjusting the pH (i.e., having a basic or acidic surfactant solution). Two embodiments of adjusting the self-assembly reaction pH are provided below in Examples 4 and 5.

Example 4

Figure 22:
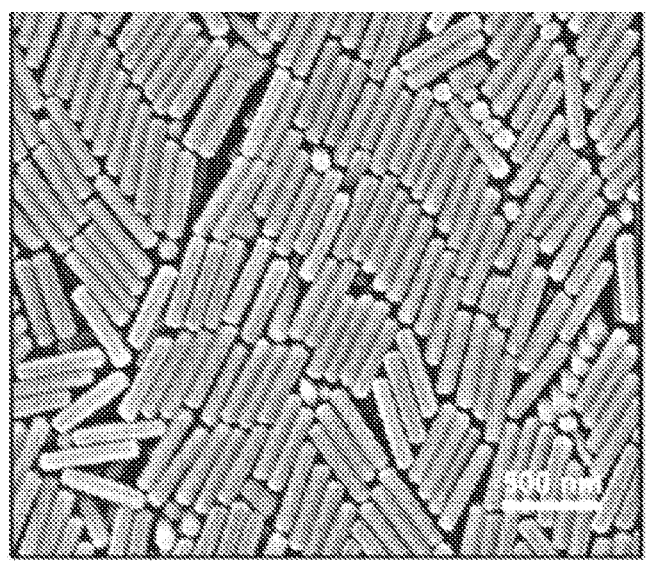
FIG. 22 is an SEM image of a plurality of hexagonal porphyrin nanorods produced using an embodiment of the method set forth in FIG. 21, in accordance with an aspect of the present disclosure.

A 0.5 ml of stock ZnTPyP solution in water (0.01 M, 0.2 M HCl) was added into 9.5 ml of SDS solution (0.01 M) with continuous stirring. NaOH was then added until a final pH of 11.1 was reached. The mixture was stirred at room temperature (25° C.) for 48 h. The nanorod-containing solution was centrifuged at 8000 rpm for 30 min and washed twice with Millipore™water to remove the surfactant. A representative SEM image of a plurality of monodisperse porphyrin nanorods so prepared is shown in FIG. 22. The average diameter of the imaged porphyrin nanorods is about 65 nm, and their average length is about 500 nm.

Example 5

Figure 23:
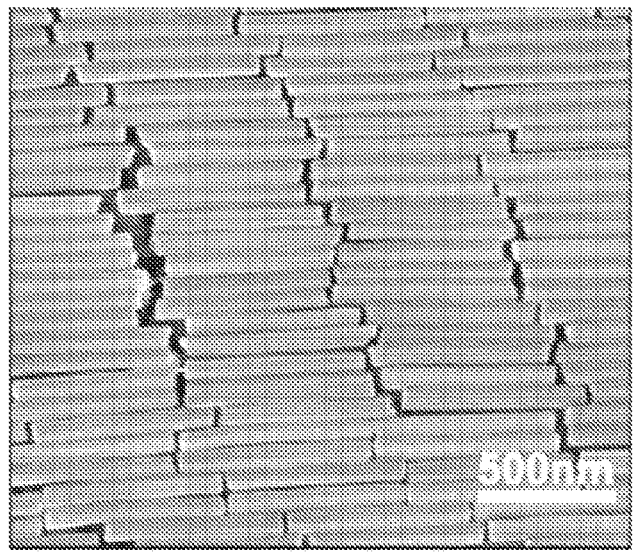
FIG. 23 is an SEM image of a plurality of long hexagonal porphyrin nanorods produced using an embodiment of the method set forth in FIG. 21, in accordance with an aspect of the present disclosure.

A 0.5 ml of stock ZnTPyP solution in water (0.01 M, 0.2 M HCl) was added into 9.5 ml of SDS solution (0.01 M) with continuous stirring. NaOH was then added until a final pH of 12.4 was reached. The mixture was stirred at room temperature (25° C.) for 48 h. The nanorod-containing solution was centrifuged at 8000 rpm for 30 min and washed twice with Millipore™water to remove the surfactant. A representative SEM image of a plurality of monodisperse porphyrin nanorods so prepared are is shown in FIG. 23. The average diameter of the imaged porphyrin nanorods is about 75 nm, and their average length is about 800 nm.

The nanostructures prepared in accordance with the present disclosure in Examples 1-5 utilize a porphyrin having a coordinated metal center. However, it should be noted that the self-assembly procedures described herein are not limited to metallated porphyrins. Rather, nanostructures having morphologies other than nanorods may be obtained using similar porphyrin structures. An example of such a method for producing other nanostructures is provided below in FIG. 24 in the context of a self-assembly reaction mixture having a pH above 7.

Figure 24:
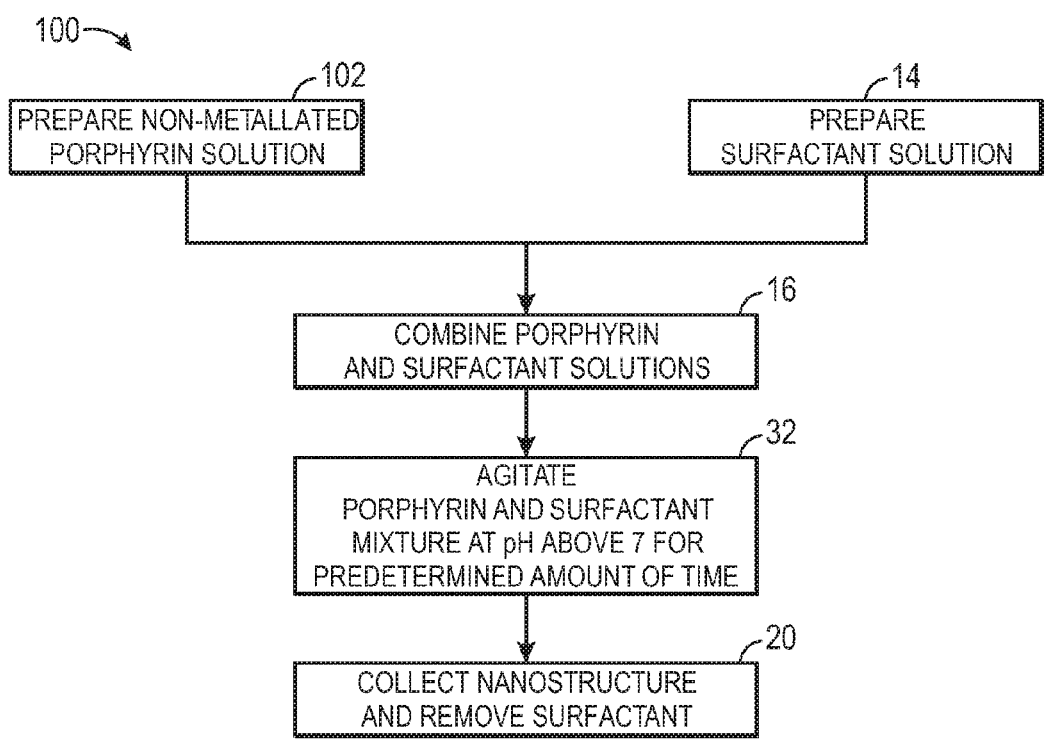
FIG. 24 is a flowchart illustrating an embodiment of the method of FIG. 4, wherein the porphyrin solution includes substantially only porphyrins that are non-metallated, in accordance with an aspect of the present disclosure.

In FIG. 24, as noted above, a method 100 using a non-metallated porphyrin solution is illustrated as a flowchart. The method 100 includes preparing a non-metallated porphyrin solution, as represented by a block 102. The preparation of the non-metallated porphyrin solution may be generally the same as described above with respect to block 12, except that a non-metallated porphyrin is utilized. The surfactant solution is prepared in accordance with block 14, and the non-metallated porphyrin solution and the surfactant solution are combined, as represented by block 16. The resulting mixture is agitated for a predetermined amount of time at a pH above 7, and the surfactant is thereafter removed to allow the collection of the formed nanostructures, as represented by blocks 32 and 20, respectively. An embodiment of method 100 is provided below in Example 6.

Example 6

A 0.5 ml of stock TPyP solution (stored longer than 48 h) in water (0.01 M, 0.2 M HCl) was added into 9.5 ml of H-678 solution (0.5 mM, containing 0.2 mmol NaOH). The resulting solution pH was 11.6. The mixture was then continuously stirred at room temperature (25° C.) for 48 h. The khaki-colored solution was then centrifuged at 8000 rpm for 20 min and washed twice with Millipore™water to remove the surfactant. An SEM image of a plurality of 3D porphyrin nanooctahedrons produced by the self-assembly reaction is provided in FIG. 25. The octahedral morphology of the 3D porphyrin nanooctahedrons may be further appreciated with reference to FIG. 25a, which is an expanded view of a portion of the image of FIG. 25. Over 90% of the plurality of 3D porphyrin nanooctahedrons in FIG. 25 have edge lengths of about 352±45 nm, as represented in the population histogram of FIG. 26. According to the present disclosure, such a plurality of 3D porphyrin nanooctahedrons may be considered a monodisperse mixture.

While the preceding examples have been provided in the context of self-assembly reaction mixtures having a pH above 7, as noted above, embodiments in accordance with the present disclosure may also include self-assembly reaction mixtures having a pH below 7. Accordingly, embodiments of method 10 from FIG. 1 wherein the reaction pH is below 7 are provided hereinbelow in the form of flowcharts and examples.

Figure 27:
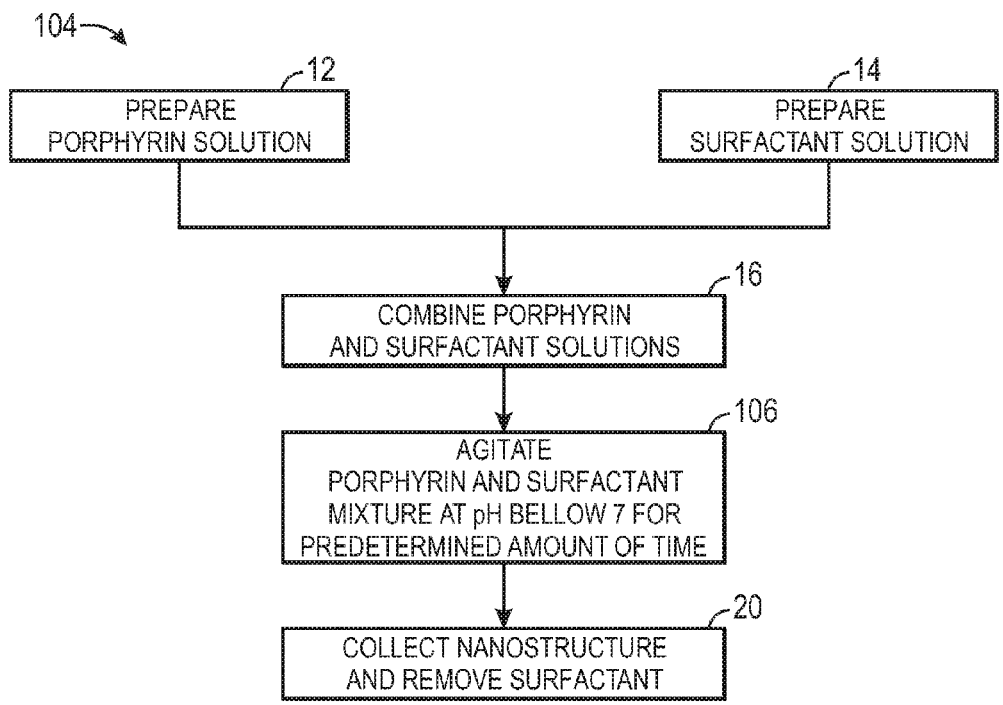
FIG. 27 is a flow chart illustrating an embodiment of the method for producing porphyrin nanostructures of FIG. 1 wherein the porphyrin-surfactant mixture is maintained at a pH below 7, in accordance with aspects of the present disclosure.

While self-assembly reaction mixtures according to the present disclosure having a pH above 7 may generally (with some exceptions) produce nanostructures having large aspect ratios such as 1D nanorods and nanowires, when the pH is below 7, nanostructures generally having 2 or 3 dimensions that are less than one micron or, alternatively, less than 500 nm in length may be produced. Examples of such nanostructures include nanodiscs, nanoplates, nanosheets, and so on. FIG. 27 provides an embodiment of a method 104 wherein the pH of the self-assembly reaction mixture is below 7 (acidic). In a similar manner to the methods described above in the context of a basic solution, the final pH may be targeted by pre-adjusting the pH of the porphyrin and/or surfactant solutions, or by adjusting the pH of the reaction mixture after combining the porphyrin and surfactant solutions. As with the embodiments described above, the manner in which the pH is adjusted may have an effect on the size and/or morphology of the nanostructure produced.

Method 104 begins in a similar manner to method 10 set forth in FIG. 1, wherein the porphyrin solution and surfactant solution are prepared, which are represented by blocks 12 and 14, respectively. As noted above, either or both of the porphyrin and surfactant solutions may be basic or acidic. For example, the porphyrin solution may be acidic while the surfactant solution is basic, or the surfactant solution may be acidic while the porphyrin solution is basic. It, should be noted that in preparing solutions according to method 104, that the surfactant solution, which contains base in many embodiments, may be less basic (i.e., closer to pH 7) than the method wherein the final pH of the solution is above 7. An example of such an embodiment is set forth below. Once the solutions are prepared, they are combined, as represented by block 16.

As noted above, to combine the solutions, the porphyrin solution may be added to the surfactant solution or the surfactant solution may be added to the porphyrin solution. Once the solutions have been combined, they are agitated for a predetermined amount of time at a pH below 7, as represented by block 106. Again, the self-assembly reaction mixture may be pH-adjusted prior to and/or after combining the porphyrin and surfactant solutions. After the predetermined amount of time has elapsed, at least a portion of the surfactant is removed and the nanostructures are collected, as represented by block 20. As an example, the mixture may be washed with purified water and/or centrifuged. Embodiments of method 104 are provided in Examples 7 and 8 below, wherein porphyrin nanodiscs are generated from Zn-TPyP and MTAB, and wherein porphyrin nanoplates are generated from Zn-TPyP and SDS, respectively.

Example 7

Figure 28:
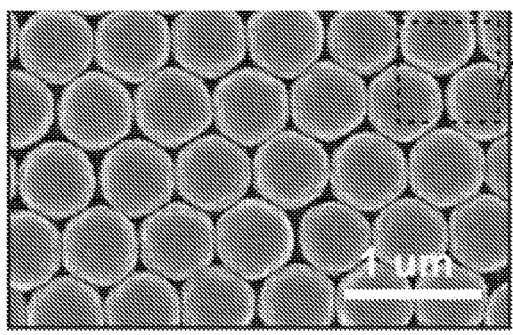
FIG. 28 is an SEM image of a plurality of porphyrin nanodiscs produced using an embodiment of the method of FIG. 24, in accordance with an aspect of the present disclosure.
Figure 28A:
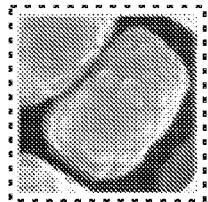
FIG. 28a is an expanded view of a portion of the SEM image of FIG. 28 showing the curved edge of one of the porphyrin nanodiscs, in accordance with an aspect of the present disclosure.
Figure 29:
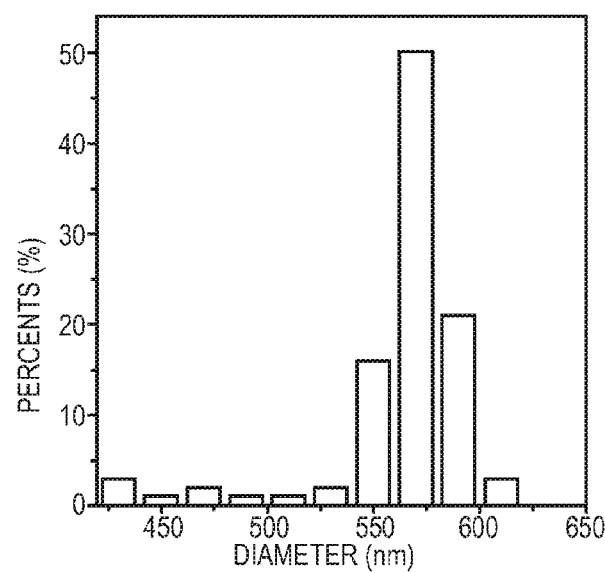
FIG. 29 is a population histogram of the diameters of the plurality of porphyrin nanodiscs in the image of FIG. 28, in accordance with an aspect of the present disclosure.

0.5 ml of a fresh stock Zn-TPyP solution (0.01 M Zn-TPyP dissolved in 0.2 M HCl solution) was quickly added into 9.5 mL of a continuously stirred aqueous solution of MTAB (0.01 M) and NaOH (0.1 mmol) at room temperature (25° C.). The pH of the resultant mixture was about 5.7. After the mixture was stirred for 30 min, the solution became green. The green solution was centrifuged at 5000 rpm and washed twice with Millipore™ water to remove the surfactant. A representative SEM image of a plurality of porphyrin nanodiscs produced by the reaction is provided in FIG. 28. The curved edges and disc shape of the porphyrin nanodiscs may be further appreciated with reference to FIG. 28a, which is an expanded view of a portion of the image of FIG. 28. Over 85% of the nanodiscs in FIG. 28 have a diameter of 560±40 nm, as represented by the histogram in FIG. 29. Such a mixture of porphyrin nanodiscs may be considered monodisperse, in accordance with an aspect of the present disclosure.

Example 8

Figure 30:
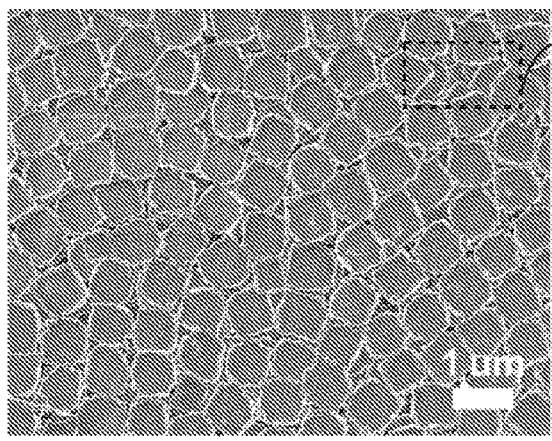
FIG. 30 is an SEM image of a plurality of porphyrin nanoplates produced using an embodiment of the method of FIG. 27, in accordance with an aspect of the present disclosure.
Figure 30A:
FIG. 30a is an expanded view of a portion of the SEM image of FIG. 30 showing the thickness of a few of the porphyrin nanoplates, in accordance with an aspect of the present disclosure.
Figure 31:
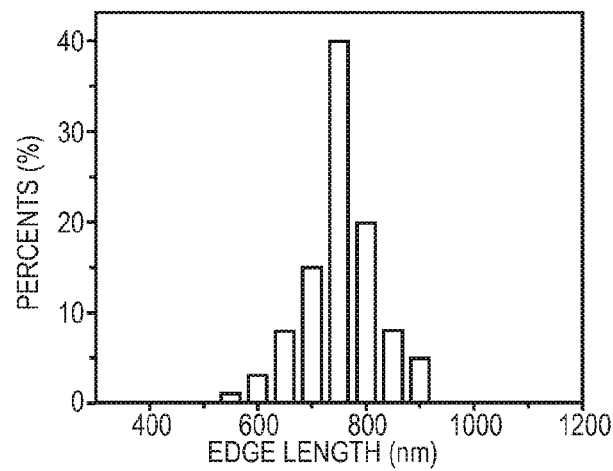
FIG. 31 is a population histogram of the edge lengths of the plurality of porphyrin nanoplates in the image of FIG. 30, in accordance with an aspect of the present disclosure.

1 ml of a stock Zn-TPyP solution (stored longer than 48 h) in water (0.01 M, 0.2 M HCl) was added into 9.5 ml of an SDS solution (0.01 M, containing 0.1 mmol NaOH) with continuous stirring. The pH of the resulting solution was about 5.7. The mixture was then stirred at room temperature (25° C.) for 24 h, resulting in a red solution. The red solution was centrifuged at 5000 rpm for 20 min and washed twice with Millipore™ water to remove the surfactant. A representative SEM image of a plurality of porphyrin nanoplates produced by the self-assembly reaction is provided in FIG. 30. The plate-like morphology of the porphyrin nanoplates may be further appreciated with reference to FIG. 30a, which is an expanded view of a portion of the image of FIG. 30. Further, as represented in the histogram of FIG. 31, over 90% of the porphyrin nanoplates in FIG. 30 have a diameter of 740±100 nm. Such a mixture of porphyrin nanoplates may be considered monodisperse, in accordance with an aspect of the present disclosure.

Figure 32:
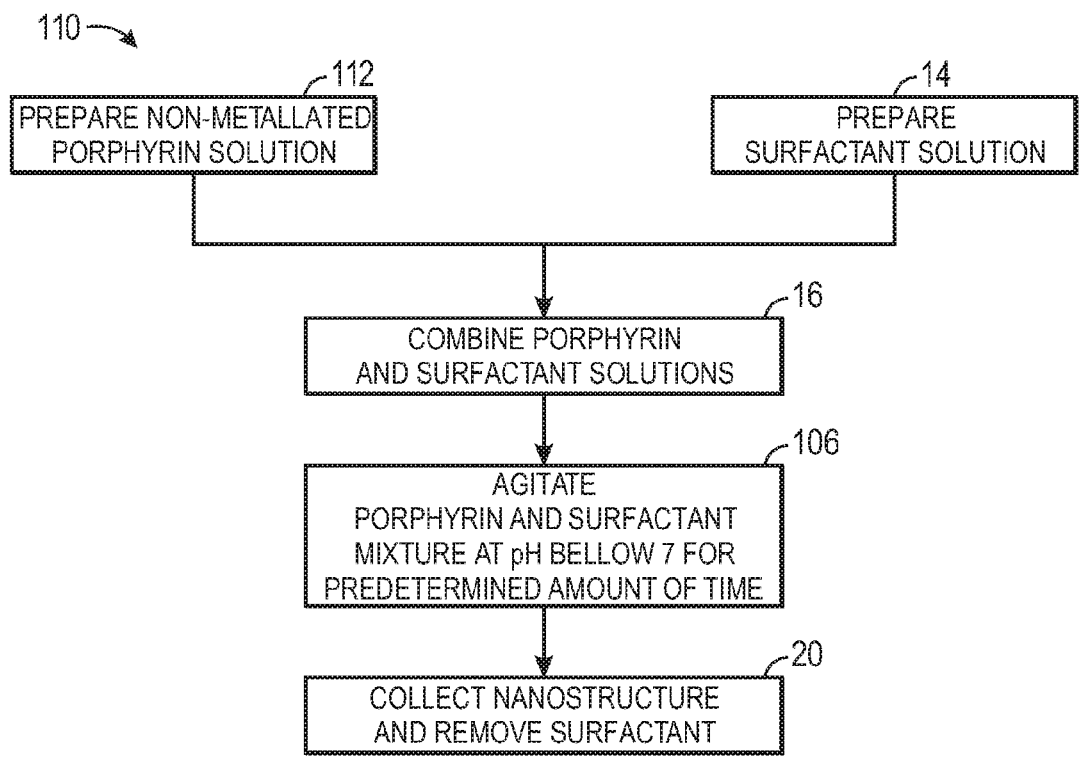
FIG. 32 is a flowchart illustrating an embodiment of the method of FIG. 27, wherein the porphyrin solution includes substantially only porphyrins that are non-metallated, in accordance with an aspect of the present disclosure.

As with self-assembly reaction mixtures having a pH above 7, the present disclosure also includes embodiments wherein the porphyrin solution includes non-metallated porphyrin molecules and the self-assembly reaction mixture is maintained below a pH of 7. FIG. 32 illustrates an embodiment of such a method 110. Method 110 generally includes similar acts to those described above with regard to method 104. Accordingly, the surfactant solution is prepared, as represented by block 14. A porphyrin solution, in accordance with the present embodiment, is prepared by dispersing/dissolving a non-metallated porphyrin in an aqueous solution, as represented by a block 112. The non-metallated porprhyin may include acidic and/or basic chemical functionalities, and may therefore be dissolved in an acidic or basic solution as determined on a porphyrin-by-porphyrin basis. The porphyrin and surfactant solutions are thereafter combined, for example by adding the porphyrin solution to the surfactant solution, as represented by block 16. The resulting mixture is then agitated for a predetermined amount of time at a pH below 7, such as at a pH of about 6.5, 6.0, 5.5, 5.0, and so on, as represented by block 106. As noted above, the pH may be pre-adjusted before mixing and/or adjusted after the solutions are combined. Once the predetermined amount of time has elapsed, at least a portion of the surfactant is removed and the nanostructures are collected, as represented by block 20. Embodiments of the method 110 are provided hereinbelow in Examples 9 and 10. In Example 9 THP, a non-metallated porprhrin, and CTAB are stirred in acidic conditions to generate ultra-thin porphyrin nanoplates. In Example 10, TCP, a non-metallated porprhyrin, is stirred with decyl sulfate in acidic conditions to generate rhombic porphyrin nanoplates.

Example 9

0.5 ml of a stock THP solution in water (0.01 M, 0.2 M NaOH) was added into 9.5 ml of a CTAB solution (0.01 M, containing 0.1 mmol HCl) with continuous stirring. The pH of the resulting mixture was 5.5. The mixture was stirred at room temperature (25° C.) for 48 h to generate a green solution. The green solution was centrifuged at 7000 rpm for 20 min and washed twice with Millipore™ water to remove the surfactant. A representative SEM image of a plurality of ultrathin porphyrin nanoplates is provided in FIG. 33, and an AFM image and corresponding height analysis are shown in FIG. 34.

Figure 33:
FIG. 33 is an SEM image of a plurality of ultrathin porphyrin nanoplates produced using an embodiment of the method of FIG. 32, in accordance with an aspect of the present disclosure.
Figure 34:
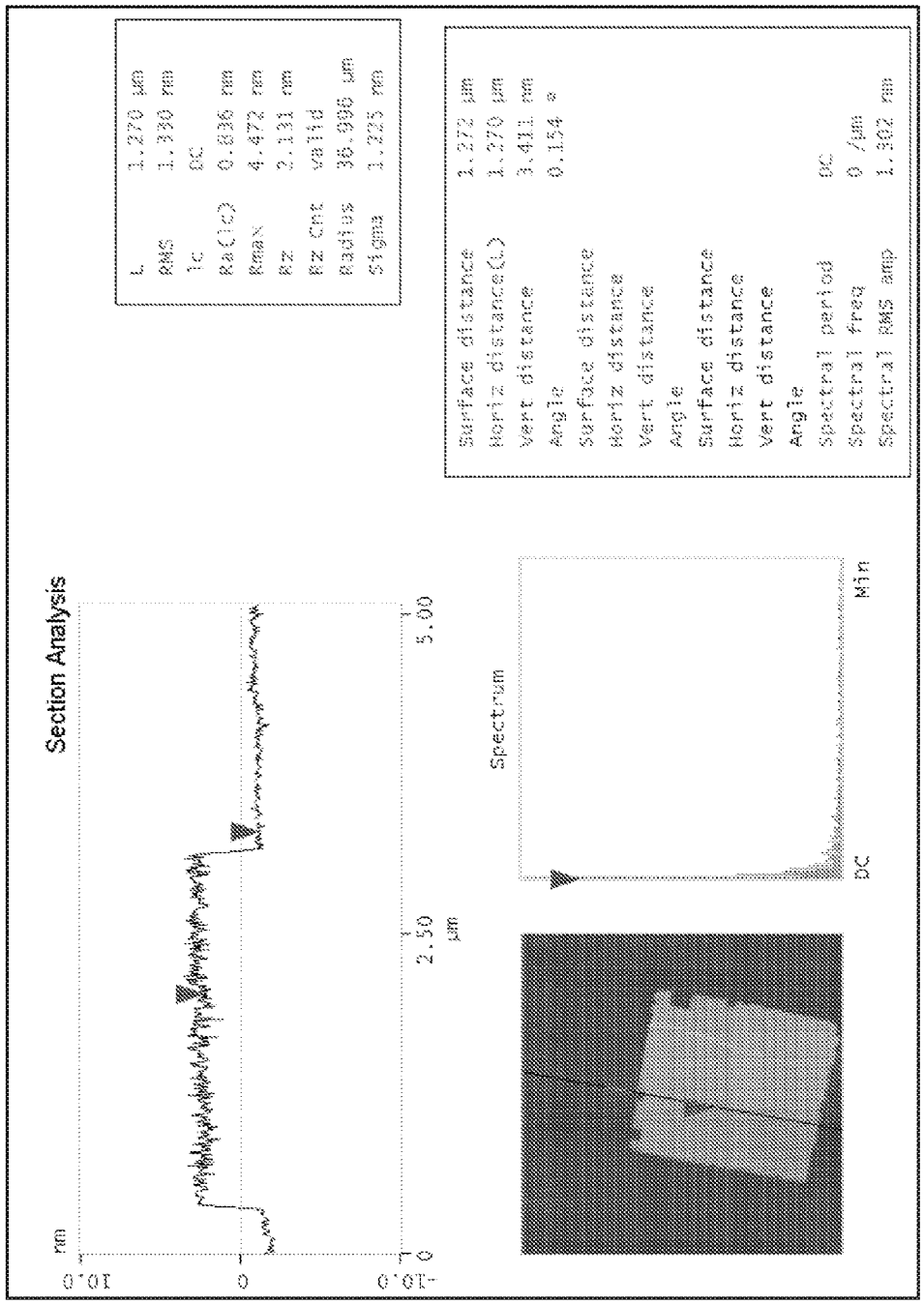
FIG. 34 is an atomic force microscope (AFM) image and height data of an ultrathin porphyrin nanoplate that is similar to the plurality of ultrathin porphyrin nanoplates in the image of FIG. 33, in accordance with an aspect of the present disclosure.

As may be appreciated in the SEM image of FIG. 33, the ultrathin porphyrin nanoplates generated by the self-assembly reaction of Example 9 are several micrometers in their length and width dimensions. However, their low contrast compared to background in the SEM image is also indicative of a structure that is only a few nanometers thick. To confirm their height, the ultrathin porphyrin nanoplates were adsorbed onto a silicon wafer and imaged using AFM. As noted above, the AFM image and the height data so generated are provided in FIG. 34. The data indeed indicates that the ultrathin porphyrin nanoplates are only a few nanometers thick (i.e., about 3.4 nm).

Example 10

Figure 35:
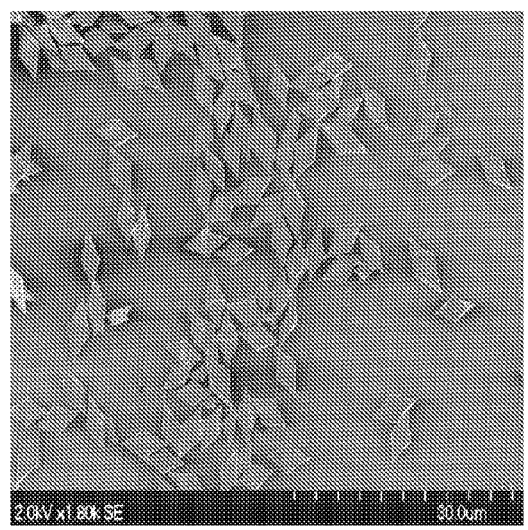
FIG. 35 is an SEM image of rhombic porphyrin nanoplates produced using an embodiment of the method of FIG. 32, in accordance with an aspect of the present disclosure.

0.5 ml of a stock TCP solution in water (0.01 M, 0.2 M NaOH) was added into 9.5 ml of a $C_{10}SO_4Na$ solution (0.01 M, containing 0.1 mmol HCl) with continuous stirring. The resulting solution pH was about 6. The mixture was stirred at room temperature (25° C.) for 24 h. Thereafter, the solution was centrifuged at 3000 rpm for 20 min and washed twice with Millipore™ water to remove the surfactant. A representative SEM image of a plurality of rhombic porphyrin nanoplates produced by the self-assembly reaction is provided in FIG. 35. As with the ultrathin porphyrin nanoplates produced in. Example 10, the rhombic porphyrin nanoplates have some dimensions (i.e., edge lengths) that are several microns or tens of microns in length. However, the rhombic porphyrin nanoplates have thicknesses of only a few nanometers.

Figure 36:
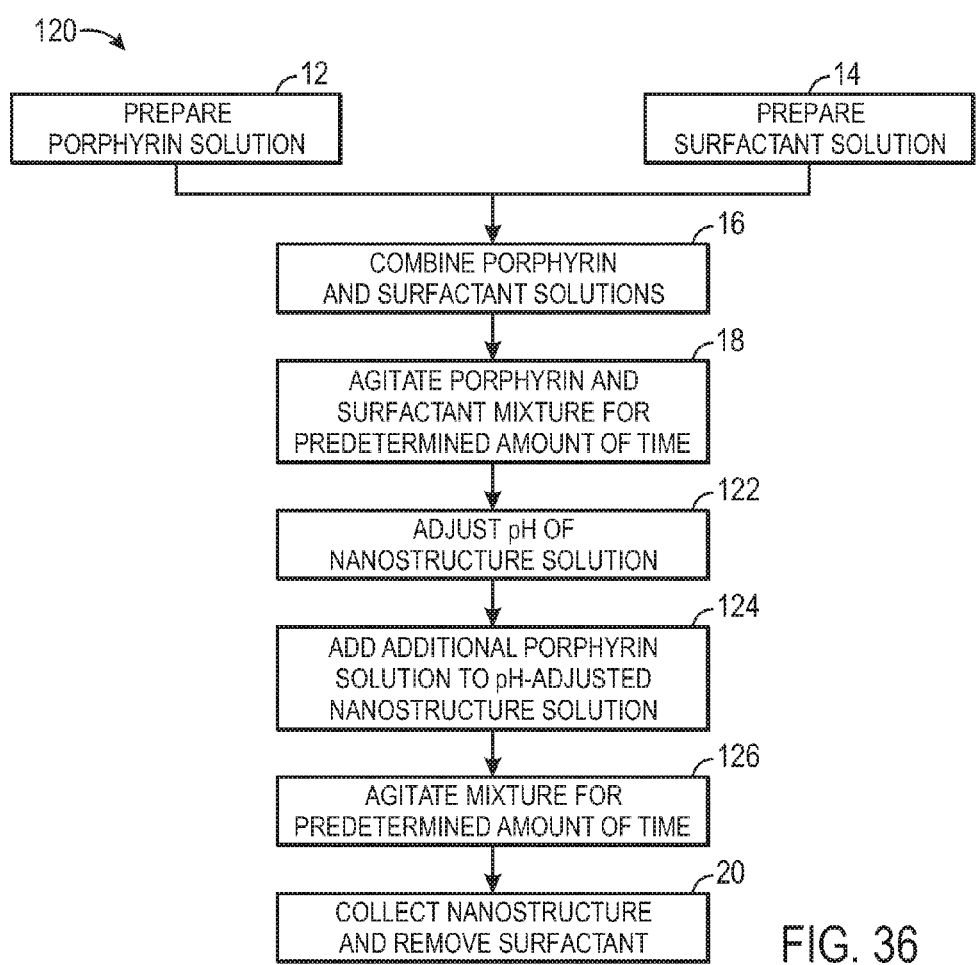
FIG. 36 is a flowchart illustrating an embodiment of a method for continuing the growth of a porphyrin nanostructure by adjusting a solution containing the porphyrin nanostructure to conditions favorable for surfactant-confined self-assembly, in accordance with an aspect of the present disclosure.
Figure 40:
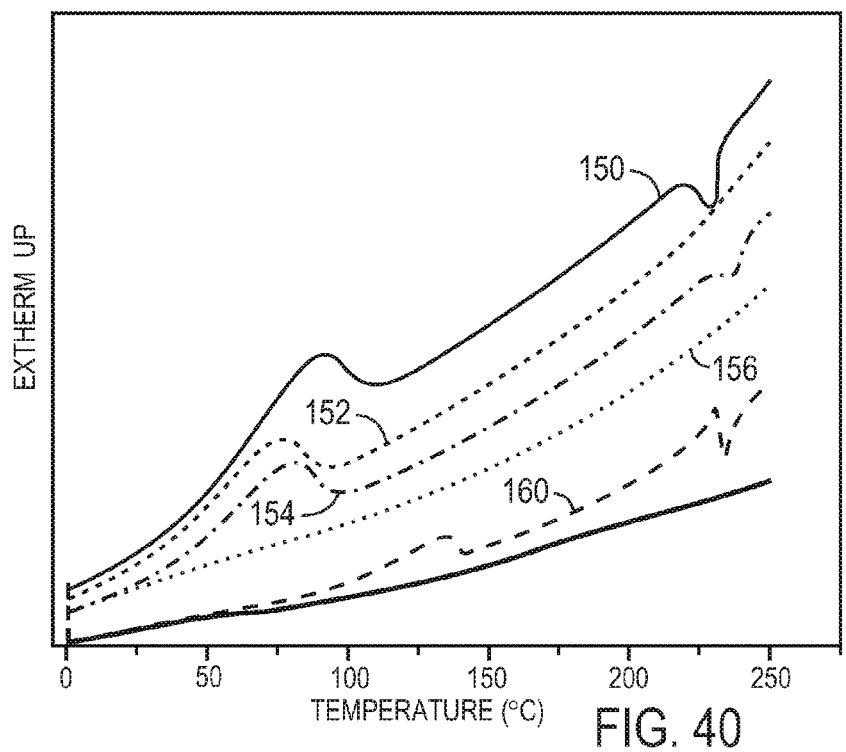
FIG. 40 is a differential scanning calorimetry (DSC) plot of hexagonal porphyrin nanorods, porphyrin nanodiscs, ultrathin porphyrin nanoplates, and porphyrin nanooctahedrons produced using varying embodiments of the method of FIG. 1, in accordance with an aspect of the present disclosure.

In accordance with another aspect of the present disclosure, as noted above, FIG. 36 illustrates, in the form of a flowchart, a method 120 for continuing the growth of a nanostructure. The nanostructure may be in a solution, for example a solution in which the nanostructure was formed. In other embodiments, the nanostructure may be in a freshly prepared solution or a stock solution of nanostructures. Furthermore, it should be noted that the growth of a nanostructure to greater than one micrometer in any dimension is also contemplated herein, and may merely be a matter of increased reaction time, increased levels of acid, base, surfactant, and/or porphyrin.

As noted above, method 120 may be applied to a solution in which a nanostructure has been generated (i.e., a self-assembly reaction), and will be discussed in such a context. Accordingly, method 120 includes many of the acts of method 10, including the preparation of porphyrin and surfactant solutions, as represented by blocks 12 and 14, respectively. Additionally, the acts represented by blocks 16 and 18 may be performed to initially generate a nanostructure.

Once the initial nanostructure has been generated, the size of the nanostructure may be increased. To ensure that the pH of the self-assembly reaction is at a desired level after adding additional porphyrin, the pH of the nanostructure solution is adjusted, as represented by a block 122. For example, a basic solution may be added to the nanostructure solution to buffer the addition of an acidic porphyrin solution. Once the pH of the nanostructure solution has been adjusted, additional porphyrin solution is added, as represented by a block 124. It should be noted that the same or different porphyrins may be used in the original porphyrin solution that is prepared and the porphyrin solution that is combined with the pH-adjusted nanostructure solution. Once additional porphyrin solution has been added, the mixture is stirred for a predetermined amount of time, as represented by a block 126. As noted above, the predetermined amount of time may be a time in which the nanostructure is expected to reach a desired size, or may be an interval time in which the self-assembly reaction mixture is sampled. Once the predetermined amount of time has elapsed, at least a portion of the surfactant may be removed and the nanostructure collected, as represented by block 20. An embodiment of method 120 is provided in Example 11, wherein a wire is grown both in length and diameter.

Example 11

To 5.0 mL of a solution containing long porphyrin nanorods prepared from Zn-TPyP and CTAB was added 15 mL of H2O and 0.2 mL of 1N HCl. To the resulting mixture was then added 0.25 mL of a Zn-TPyP solution (0.01 M, 0.2M HCl). The pH of the resulting reaction mixture was 11.3. The mixture was stirred for 48 h, then centrifuged at 7000 rpm for 20 min and washed twice with Millipore™ water to remove the surfactant. Representative SEM images of a plurality of porphyrin nanorods before performing the continued growth reaction and after performing the continued growth reaction are provided in FIGS. 37 and 38, respectively. Indeed, the length and the diameter of the porphyrin nanorods changed from an average of about 2.2 µm and 92 nm, respectively, to an average of about 2.6 µm and 115 nm, respectively.

In view of the foregoing, it should be noted that the methods in accordance with the present disclosure generate porphyrin nanostructures having a wide variety of dimensions and morphologies. For example, as described above, the present methods may generate 1D nanostructures such as long nanowires and porphyrin nanorods, 2D nanostructures such as porphyrin nanodiscs and porphyrin nanoplates, and 3D nanostructures such as porphyrin nanooctahedrons. As noted above, these nanostructures may have properties that make them useful for a variety of implementations, such as in fuel cells and/or electronic devices. As an example of their unique properties, several physical, optical, and chemical properties are described hereinbelow with respect to FIGS. 39-46.

FIG. 39 contains $N_2$ sorption data for a variety of nanostructures synthesized in accordance with the presently disclosed methods, specifically nanodiscs, ultrathin nanorods, hexagonal rods, and nanoplates synthesized from Zn-TPyP. The $N_2$ sorption data was measured on a Micromeritics ASAP 2010 system. In a standard experiment, a powder of the nanostructure was placed into a glass container and sealed using Viton O-rings. The container was degassed for 24 h at 50° C. under vacuum. The $N_2$ sorption isotherms were then obtained at 77K.

In FIG. 39, a line 130 represents the $N_2$ adsorption of porphyrin nanodiscs while a line 132 represents their $N_2$ desorption. A line 134 represents the $N_2$ adsorption of long porphyrin nanowires, and a line 136 represents their $N_2$ desorption. A line 138 represents the $N_2$ adsorption of hexagonal porphyrin nanorods, and a line 140 represents their $N_2$ desorption. A line 142 represents the $N_2$ adsorption of porphyrin nanoplates, and a line 144 represents their $N_2$ desorption. It should be noted that the nanorods exhibit characteristic type I isotherms (according to IUPAC classification), which is indicative that they are microporous. However, the lines 132 and 134 corresponding to the nanodiscs indicate that the nanodiscs have type IV isotherms, which is indicative of a mesoporous structure. In this regard, the nanodiscs are highly porous and have an increased ability to store $N_2$ compared to the other nanostructures, as represented by the difference between the $N_2$ adsorption and desorption traces. Indeed, the porphyrin nanodiscs appear to retain much of their adsorbed $N_2$ even after considerable pressure reduction. Conversely, the porphyrin nanoplates do not exhibit any appreciable $N_2$ adsorption, which may be due to a combination of porosity, surface area, and average pore size.

Using similar sorption data obtained for a variety of nanostructures, the porosity, surface area, and pore size obtained by Brunauer, Emmett, and Teller (BET) theory for each of the nanostructures is provided in Table 2 below. It will be appreciated with reference to Table 2 that the porphyrin nanodiscs exhibit the highest surface area and the highest levels of porosity. The data in Table 2 also indicates that, like the porphyrin nanodiscs, the ultrathin porphyrin nanorods and hexagonal porphyrin nanorods may also be useful in gas sorption implementations.

TABLE 2

| Porphryin Nanostructure | Porosity (%) | Surface Area ($m^2/g$) | Pore Size (nm) |
| --- | --- | --- | --- |
| nanodiscs | 40.4 | 457 | 3.58 |
| ultra thin nanorods | 34.3 | 371 | 3.7 |
| hexagonal nanorods | 20.1 | 327 | 2.46 |
| nanoplates | 8.9 | 30.6 | 11.2 |
| rectangular nanorods | 8.2 | 32.8 | 22 |
| nanooctahedrons | 7.6 | 32.9 | 9.2 |

The phase behavior and the thermal stability of various nanostructures produced in accordance with the present disclosure may also make them attractive for use in devices or systems that experience temperature variations, including high temperature conditions. As an example, a differential scanning calorimetry (DSC) plot is provided in FIG. 40 and a thermogravimetric analysis (TGA) plot is provided in FIG. 41. Specifically, FIG. 40 includes a DSC curve 150 for porphryin nanodiscs, a DSC curve 152 for rectangular porphyrin nanorods, a DSC curve 154 for hexagonal porphyrin nanorods, a DSC curve 156 for porphyrin nanooctahedrons produced from a non-metallated porphyrin, a DSC curve 158 for ultrathin porphryin nanoplates, and a DSC curve for porphryin nanooctahedrons produced from a metallated porphyrin.

As may be appreciated from the DSC curves, the porphyrin nanodiscs, rectangular porphyrin nanorods, and hexagonal porphyrin nanorods all exhibit a crystallization peak between 75 and 95° C. Likewise, the ultrathin porphyrin nanoplates exhibit such a peak at about 136° C. Moreover, the porphyrin nanodiscs, hexagonal porphyrin nanorods, and the ultrathin porphyrin nanoplates all exhibit melting temperatures between about 229° C. and 236° C., indicating that they may be used up to such temperatures in solid devices. However, the rectangular porphyrin nanorods do not appear to exhibit a melting point within the scanned range. Furthermore, the octahedrons do not exhibit any phase changes within the scanned range, which may be due to their high degree of crystallinity.

Figure 41:
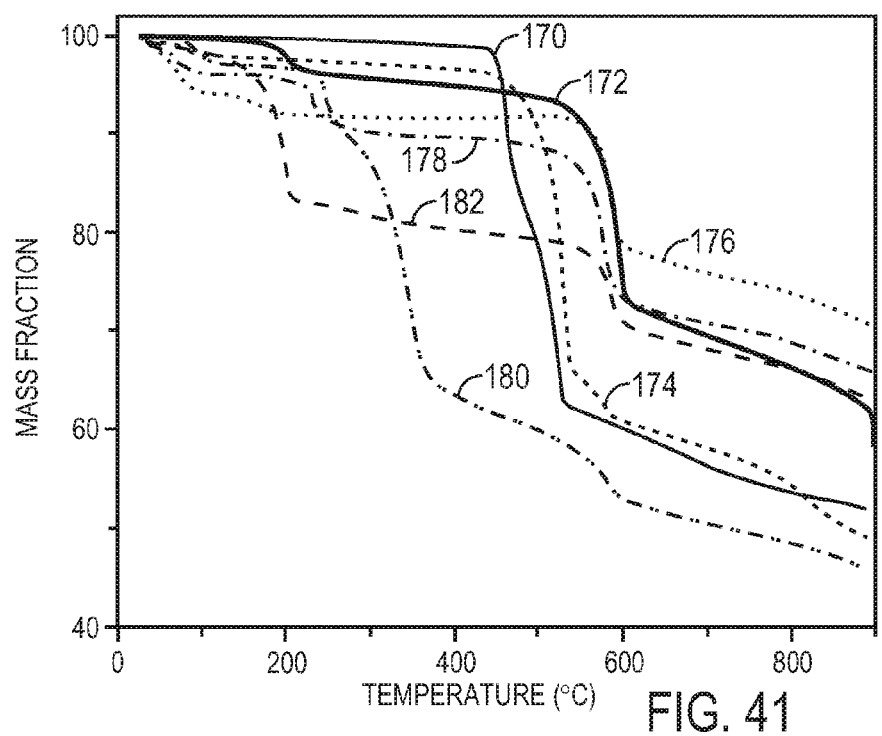
FIG. 41 is a thermogravimetric analysis plot of porphyrin nanodiscs, porphyrin nanooctahedrons, hexagonal porphyrin nanorods with and without pre-adsorbed NO, and ultrathin porphyrin nanoplates produced using varying embodiments of the method of FIG. 1, in accordance with an aspect of the present disclosure.

FIG. 41, as noted above, includes TGA data. Specifically, the TGA data includes a TGA curve 170 for porphyrin nanooctahedrons produced from a non-metallated porphyrin, a TGA curve 172 for rectangular porphyrin nanorods, a TGA curve 174 for porphyrin nanooctahedrons produced from a metallated porphyrin, a TGA curve 176 for hexagonal porphyrin nanorods, a TGA curve 178 for porphyrin nanodiscs, a TGA curve 180 for ultrathin porphyrin nanoplates, and a TGA curve 182 for hexagonal porphyrin nanorods having pre-adsorbed nitric oxide (NO). The TGA curves all indicate thermal stability up to at least about 325° C. before carbonization occurs. Moreover, TGA curve 182 for the hexagonal porphyrin nanorods having pre-adsorbed NO indicates that the NO that is adsorbed in the nanorods is released above about 150° C.

Figure 42:
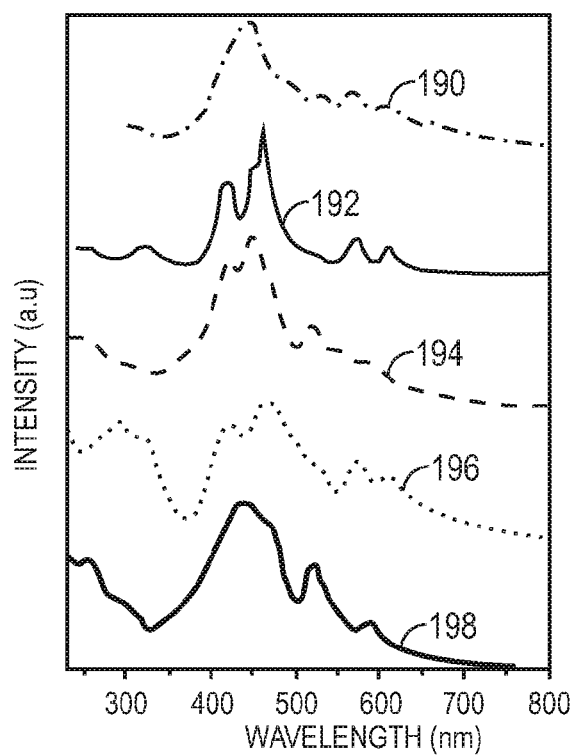
FIG. 42 is a combined UV/Vis spectrum comparing the absorbance of porphyrin nanoplates, hexagonal porphyrin nanorods, rectangular porphyrin nanorods, and porphyrin nanooctahedrons produced using varying embodiments of the method of FIG. 1, in accordance with an aspect of the present disclosure.
Figure 43:
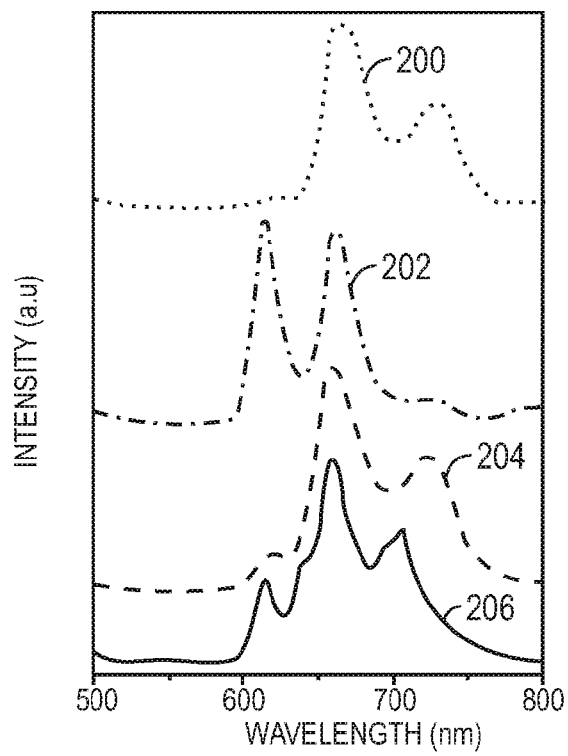
FIG. 43 is a combined fluorescence spectrum comparing the absorbance of porphyrin nanoplates, hexagonal porphyrin nanorods, rectangular porphyrin nanorods, and porphyrin nanooctahedrons produced using varying embodiments of the method of FIG. 1, in accordance with an aspect of the present disclosure.

As noted above, the porphyrin nanostructures produced by the methods described herein may exhibit unique optical properties that enable their use in photovoltaics, optics, and other areas. FIGS. 42 and 43 include UVN is absorbance data and fluorescence data, respectively, for several porphyrin nanostructures synthesized from Zn-TPyP or TPyP. Specifically, FIG. 42 includes UVN is data for porphyrin nanoplates 190, for hexagonal porphyrin nanorods 192, for rectangular porphyrin nanorods 194, for porphyrin nanooctahedrons produced from a non-metallated porphyrin 196, and for porphyrin nanooctahedrons produced from a metallated porphyrin 198. Additionally, it should be noted that the porphyrin nanodiscs retained the optical property of the individual porphyrin molecules. In a general sense, the Zn-TPyP or TPyP nanostructures exhibit a much broader absorption spectrum than their respective individual porphyrins, ranging from the visible area to the near infrared area.

The broad range of absorbance by the porphyrin nanostructures described above may be utilized for various photovoltaic processes. Indeed, as an example, hexagonal porphyrin nanorods are insulating in the absence of light, but upon illumination with 325 nm light, distinct photoconduction phenomena is observed. Moreover, the hexagonal porphyrin nanorods exhibit a rapid response (<100 ms) of the current when the light is turned on or off.

As noted above, FIG. 43 includes fluorescence data for some of the porphyrin nanostructures synthesized using Zn-TPyP or TPyP. Specifically, FIG. 43 includes fluorescence data collected for porphyrin nanoplates 200, for hexagonal porphyrin nanorods 202, for rectangular porphyrin nanorods 204, and for porphyrin nanooctahedrons produced from a non-metallated porphyrin 206. As may be appreciated from the data, the emission spectra generally range between 600 and 750 nm. It should be noted that the data for the porphyrin nanostructures display different optical features from that of single Zn-TPyP molecules, such as extra emission peaks and shifted emission peaks. These observations may be due to the collective optical behavior resulting from the assembly of individual Zn-TPyP molecules (i.e., a collective behavior).

Figure 44:
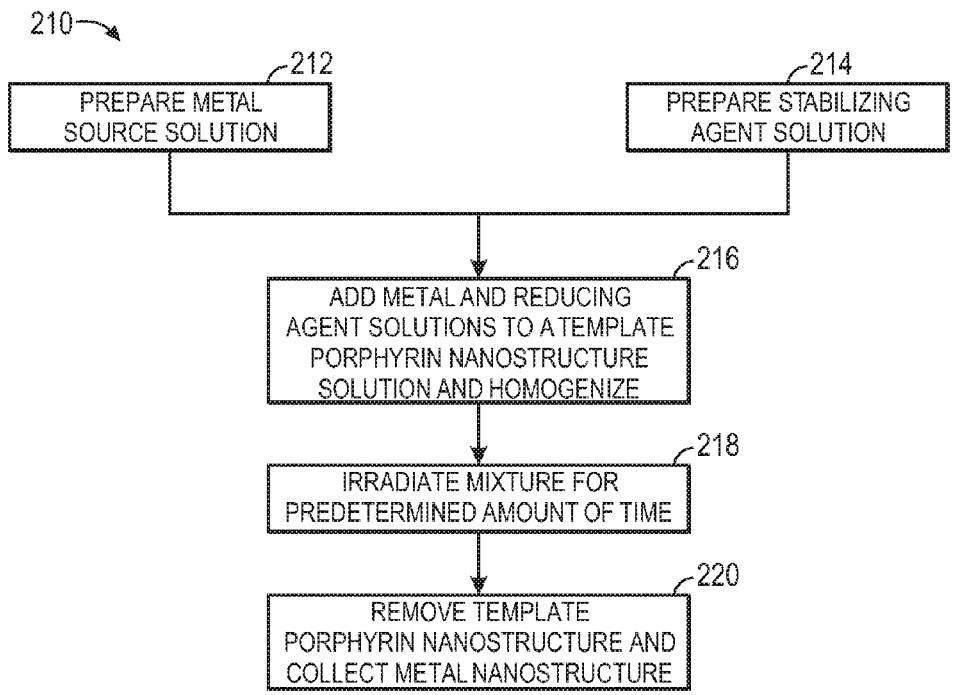
FIG. 44 is a flowchart illustrating an embodiment of a method for producing metal nanostructures from porphyrin nanostructures by photo-induced reduction, in accordance with an aspect of the present disclosure.

In addition to their unique absorbance and fluorescence behavior, porphyrin nanostructures generated in accordance with the present disclosure may be utilized for photochemical processes. As an example, a porphyrin nanostructure may be used to synthesize a metallic nanostructure by photocatalyzing the reduction of a metal in solution. FIG. 44 illustrates a flowchart of such a method 210 for generating metallic nanostructures using porphyrin nanostructures as photocatalysts. Specifically, the method 210 includes the preparation of a metal source solution, as represented by a block 212. The metal source solution can be any aqueous solution of a reducible metal (i.e., a metal ion). As an example, the metal may be a transition metal such as Pd, Pt, Fe, Cu, Ag, Ni, and so on. In addition to the metal source solution, a stabilizing agent solution is also separately prepared, as represented by a block 214. The stabilizing agent is generally an aqueous solution, and may generally include an electron-donating species, such as the conjugate base of a carboxylic acid. In some embodiments, the agent may be ascorbic acid. Once the solutions have been prepared, they are added to a solution containing a porphyrin nanostructure and homogenized, as represented by a block 216. In some embodiments, the porphyrin nanostructure solution may be an aqueous solution in which the nanostructures are dispersed. The homogenized solution may then be irradiated using a suitable wavelength of light, as represented by a block 218, in order to catalyze reduction of the metal, which is deposited on the surface of the porphyrin nanostructure. In this way, the porphyrin nanostructure acts as a template for the formation of the metallic nanostructure. In some embodiments, the source of light may be an incandescent lamp, or a lamp that may be filtered to emit a certain wavelength. Once the mixture has been irradiated for a predetermined amount of time, a metallic nanostructure that at least partially envelopes the porphyrin nanostructure may be formed. If desired, the porphyrin nanostructure that acts as a template may then be removed, for example by dissolving the porphyrin nanostructure in a solution of sufficient acidity or basicity, as represented by a block 220. As the metal nanostructures may have structures that are substantially the same as the porphyrin nanostructures, the metal nanostructures may be monodisperse. An embodiment of method 210 is provided below in Example 12, wherein a plurality of hexagonal porphyrin nanorods are used to form hollow platinum nanowires.

Example 12

Figure 45:
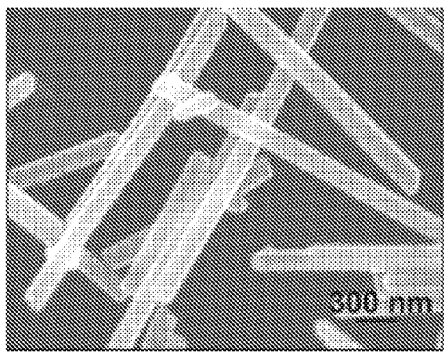
FIG. 45 is an SEM image of a plurality of nanowires having a porphyrin inner core and a metallic shell produced using an embodiment of the method of FIG. 44, in accordance with an aspect of the present disclosure.
Figure 46:
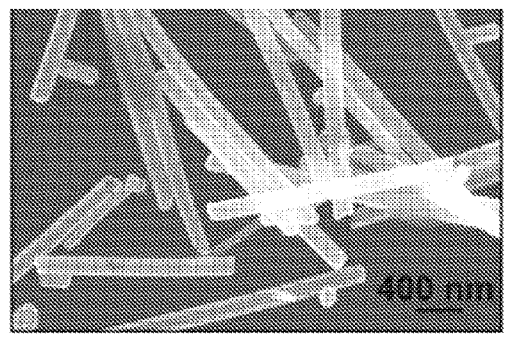
FIG. 46 is an SEM image of a plurality of hollow metallic nanowires generated using an embodiment of the method of FIG. 44, in accordance with an aspect of the present disclosure.

0.5 mL of a $K_2PtCl_4$ stock solution (20 mM Pt) and 0.5 mL of an ascorbic acid stock solution (0.2 M) were added to a 20-ml glass vial containing 10-ml of long Zn-TPyP nanowires (0.1 mg/mL). The reaction mixture was then sonicated in an ultrasound bath to ensure homogeneity. The solution was then irradiated with incandescent light (800 nmol $cm^{-2}$ $s^{-1}$) for 30 min. Hollow Pt wires were obtained after the long Zn-TPyP nanowires were removed with 1N HCl. FIG. 45 is an SEM image of the long Zn-TPyP nanowires having Pt nanowires disposed thereon, and FIG. 46 is an SEM image of the Pt nanowires after having removed the long Zn-TPyP nanowires with 1N HCl.

The specific embodiments described above have been shown by way of example, and it should be understood that these embodiments may be susceptible to various modifications and alternative forms. It should be further understood that the claims are not intended to be limited to the particular forms disclosed, but rather to, cover all modifications, equivalents, and alternatives falling within the spirit and scope of this disclosure.

What is claimed is:

1. A method for producing porphyrin nanostructures, comprising:
preparing a porphyrin solution comprising porphyrin molecules and a surfactant solution comprising surfactant molecules, wherein the porphyrin solution and the surfactant solution are aqueous solutions having different pH;
combining the porphyrin solution and the surfactant solution to neutralize the solutions and produce a porphyrin-surfactant mixture, wherein the concentration of the surfactant molecules within the porphyrin-surfactant mixture is above the critical micelle concentration of the surfactant molecules; and
agitating the porphyrin-surfactant mixture for an amount of time to produce a plurality of porphyrin nanostructures.

2. The method of claim 1, wherein the porphyrin solution comprises an acidic aqueous solution and the surfactant solution comprises a basic aqueous solution, and the porphyrin-surfactant mixture is at a pH above 7.

3. The method of claim 1, wherein the porphyrin solution comprises an acidic aqueous solution and the surfactant solution comprises a basic aqueous solution, and the porphyrin-surfactant mixture is at a pH below 7.

4. The method of claim 1, wherein the porphyrin solution comprises a basic aqueous solution and the surfactant solution comprises an acidic aqueous solution, and the porphyrin-surfactant mixture is at a pH above 7.

5. The method of claim 1, wherein the porphyrin solution comprises a basic aqueous solution and the surfactant solution comprises an acidic aqueous solution, and the porphyrin-surfactant mixture is at a pH below 7.

6. The method of claim 1, comprising removing at least a portion of the surfactant molecules from the porphyrin-surfactant mixture after agitating the porphyrin-surfactant mixture for the amount of time to isolate the plurality of porphyrin nanostructures from the portion of the surfactant molecules.

7. The method of claim 1, wherein agitating the porphyrin-surfactant mixture for an amount of time comprises self-assembling at least a portion of the porphyrin molecules within a micelle formed by at least a portion of the surfactant molecules.

8. The method of claim 1, wherein the molar ratio of surfactant molecules to porphyrin molecules is at least about 3 to 1.

9. The method of claim 1, wherein the plurality of porphyrin nanostructures comprise 1D nanostructures.

10. The method of claim 1, wherein the plurality of porphyrin nanostructures comprise 2D nanostructures.

11. The method of claim 1, wherein the plurality of porphyrin nanostructures comprise 3D nanostructures.

12. The method of claim 1, wherein the porphyrin molecules are each coordinated to a metal.

13. The method of claim 12, wherein the metal comprises Zn, Fe, Cu, or Pt.

14. The method of claim 1, wherein the porphyrin molecules comprise more than one type of porphyrin.

15. The method of claim 1, wherein the porphyrin molecules are not coordinated to a metal.

16. The method of claim 1, wherein the surfactant molecules comprise an anionic surfactant, a non-ionic surfactant, a cationic surfactant, or any combination thereof.

17. The method of claim 1, wherein the porphyrin molecules comprise a porphine inner core and at least two pendant moieties capable of coordinating to a metal.

18. The method of claim 1, comprising adjusting the pH of the porphyrin-surfactant mixture after the porphyrin solution and the surfactant solution are combined.

* * * * *